(12) United States Patent
Haffner et al.

(10) Patent No.: US 6,984,650 B2
(45) Date of Patent: Jan. 10, 2006

(54) USE OF FXR LIGANDS

(75) Inventors: Curt Dale Haffner, Durham, NC (US); Patrick Reed Maloney, Durham, NC (US); Timothy Mark Willson, Durham, NC (US); Steven Gerard Blanchard, Durham, NC (US); Steven A. Kliewer, Dallas, TX (US); Jurgen M. Lehmann, San Carlos, CA (US); Derek James Parks, Durham, NC (US); Julie Beth Stimmel, Durham, NC (US)

(73) Assignee: Smithkline Beecham Corporation, Philadelphia, PA (US)

(*) Notice: Subject to any disclaimer, the term of this patent is extended or adjusted under 35 U.S.C. 154(b) by 53 days.

(21) Appl. No.: 10/637,190

(22) Filed: Aug. 8, 2003

(65) Prior Publication Data

US 2004/0048316 A1 Mar. 11, 2004

Related U.S. Application Data

(63) Continuation of application No. 09/868,397, filed as application No. PCT/US99/30947 on Dec. 22, 1999, now Pat. No. 6,639,078.
(60) Provisional application No. 60/135,097, filed on Dec. 23, 1998.

(51) Int. Cl.
*A61K 31/415* (2006.01)

(52) U.S. Cl. ....................... 514/340; 514/378
(58) Field of Classification Search ................. 514/340, 514/378

See application file for complete search history.

(56) References Cited

FOREIGN PATENT DOCUMENTS

| EP | 0245825 | 11/1987 |
|---|---|---|
| WO | WO 91/15479 | 10/1991 |
| WO | WO 96/21742 | 7/1996 |
| WO | WO 97/04774 | 2/1997 |
| WO | WO 99/18124 | 4/1999 |
| WO | WO 99/50664 | 10/1999 |
| WO | WO 00/25134 | 5/2000 |
| WO | WO 00/39070 | 7/2000 |
| WO | WO 00/57915 | 10/2000 |

OTHER PUBLICATIONS

Comment of Saul J. Karpen, M.D., Ph.D. on Parks et al., *Hepatology* 30:4 1107–1109 (Oct. 1999).
Knowles et al., "Action of 5-isoxazolones on enamines," *J. Chem. Soc, Perk. Trans. 1* 9–10:1240–1243 (1972). (abstract only).

Krey et al., "Fatty acids, eicosanoids, and hypolipidemic agents identified as ligands of peroxisome proliferator–activated receptors by coactivator–dependent receptor ligand assay," *Molecular Endocrinology* 11(6):779–791 (Jun. 1997).
Makishima et al., "Identification of a nuclear receptor for bile acids," *Science* 284:1362–1365 (1999).
Maloney et al., "Identification of a chemical tool for the orphan nuclear receptor FXR," *Journal of Medicinal Chemistry* 43(16):2971–2974 (Aug. 2000).
Nichols et al., "Development of a scintillation proximity assay for peroxisome proliferator–activated receptor γ ligand binding domain," *Analytical Biochemistry* 257(2):112–119 (Mar. 1998).
Nolte et al., "Ligand binding and co–activator assembly of the peroxisome proliferator–activated receptor–γ," *Nature* 395:137–143 (Sep. 1998).
Parks et al., Bile acids: natural ligands for an orphan nuclear receptor,: *Science* 284:1365–1368 (1999).
Yao et al., "The nuclear hormone receptor coactivator SRC–1 is a specific target of p300," *Proc. Natl. Acad. Sci. USA* 93:10626–10631 (1996).
Zhou et al., "Nuclear receptors have distinct affinities for coactivators: characterization by fluorescence resonance energy transfer," *Molecular Endocrinology* 12(10):1594–1604 (Oct. 1998).
Goldstein et al., *Regulation of the mevalonate pathway*, Nature 343:425–430 (Feb. 1, 1990).
Fujita e al., *Moleculare cloning, expression, and characterization of human intestinal 15–kDa protein*, European J. Biochemistry 233:406–413 (1995).
Kanda et al., *Regulation of expression of human intestinal bild acid–binding protein in Caco–2 cells*, Biochem Journal 330:261–265 (1998).
Forman et al., *Identification of a Nuclear Receptor that is Activated by Farnesol Metabolites*, Cell 81:687–693 (Jun. 2, 1995).
Zhou *Nuclear Receptors Have Distinct Affinities for Coativators: Characterization by fluorescence Resonance Energy Transfer*, Molecular Endocrinology 12:1594–1604 (1998).
Craddock et al., *Expression and transport properties of the human ileal and renal sodium–dependent bile acid transporter*, American Physiological Society 274:157–169 (1998).

*Primary Examiner*—Joseph K. McKane
*Assistant Examiner*—Rebecca Anderson
(74) *Attorney, Agent, or Firm*—Virginia G. Campen

(57) ABSTRACT

The present invention includes nuclear receptor heterodimer and nuclear receptor-coactivator peptide assays for identifying ligands for nuclear receptors, utilizing scintillation proximity and fluorescence resonance energy transfer (FRET), and methods of using identified ligands.

2 Claims, 7 Drawing Sheets

USE OF FXR LIGANDS

RELATED APPLICATIONS

This application is a continuation of application Ser. No. 09/868,397 filed Jun. 18, 2001, now U.S. Pat. No. 6,639,078, which is a United States National Phase Application of International Application No. PCT/US99/30947 filed Dec. 22, 1999, which claims priority from Provisional Application No. 60/135,097 filed Dec. 23, 1998.

BACKGROUND OF THE INVENTION

Farnesoid X Receptor (FXR) is an orphan nuclear receptor initially identified from a rat liver cDNA library (8) that is most closely related to the insect ecdysone receptor. FXR is a member of the nuclear receptor family of ligand-activated transcription factors that includes receptors for the steroid, retinoid, and thyroid hormones (6). Northern and in situ analysis show that FXR is most abundantly expressed in the liver, intestine, kidney, and adrenal (8;22). FXR binds to DNA as a heterodimer with the 9-cis retinoic acid receptor RXR. The FXR/RXR heterodimer preferentially binds to response elements composed of two nuclear receptor half sites of the consensus AG(G/T)TCA organized as an inverted repeat and separated by a single nucleotide (IR-1 motif (8). An early report showed that rat FXR is activated by micromolar concentrations of farnesoids such as farnesol and juvenile hormone (8). However, these compounds failed to activate the mouse and human FXR, leaving the nature of the endogenous FXR ligand in doubt. The present invention demonstrates that several naturally-occurring bile acids bind and activate FXR at physiological concentrations (see also recent publications 17; 19; 24). As discussed in the present invention, the bile acids that serve as FXR ligands include chenodeoxycholic acid (CDCA), deoxycholic acid (DCA), lithocholic acid (LCA), and the taurine and glycine conjugates of these bile acids.

Bile acids are cholesterol metabolites that are formed in the liver and secreted into the duodenum of the intestine, where they have important roles in the solubilization and absorption of dietary lipids and vitamins. Most bile acids (~95%) are subsequently reabsorbed in the ileum and returned to the liver via the enterohepatic circulatory system. The conversion of cholesterol to bile acids in the liver is under feedback regulation: Bile acids down-regulate the transcription of cytochrome P450 7a (CYP7a), which encodes the enzyme that catalyzes the rate limiting step in bile acid biosynthesis. There are data to suggest that FXR is involved in the repression of CYP7a expression by bile acids, although the precise mechanism remains unclear (21). In the ileum, bile acids induce the expression of the intestinal bile acid binding protein (IBABP), a cytoplasmic protein which binds bile acids with high affinity and may be involved in their cellular uptake and trafficking. Two groups have now demonstrated that bile acids mediate their effects on IBABP expression through activation of FXR, which binds to an IR-1 type response element that is conserved in the human, rat, and mouse IBABP gene promoters (14; 17). Thus FXR is involved in both the stimulation (IBABP) and the repression (CYP7a) of target genes involved in bile acid and cholesterol homeostasis.

The present invention has made the useful discovery of ligands for FXR as well as methods of determining genes regulated by FXR interaction and affecting those genes. Thus this discovery provides methods of regulating bile acid and cholesterol homeostasis, fatty acid absorption, and protein and carbohydrate digestion.

SUMMARY OF THE INVENTION

The present invention provides a method of identifying compounds for the treatment of diseases or disorders modulated by FXR, comprising the step of determining whether the compound interacts directly with FXR, wherein a compound that interacts directly with FXR is a compound for the treatment.

The present invention also provides a compound that binds Farnesoid X receptor wherein the compound is of the following formula (II):

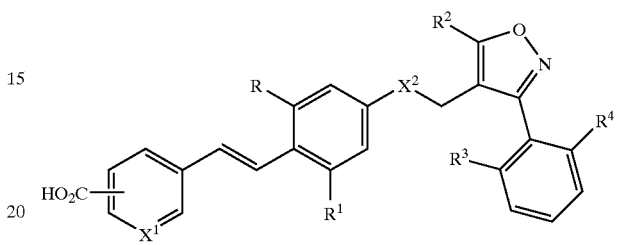

wherein $X^1$ is CH or N; $X^2$ is O or NH; R and $R^1$ may independently be H, lower alkyl, halogen, or $CF_3$; $R^2$ is lower alkyl; $R^3$ and $R^4$ may independently be H, lower alkyl, halogen, $CF_3$, OH, O-alkyl, or O-polyhaloalkyl.

The present invention further provides a method of modulating a gene whose expression is regulated by FXR in a mammal comprising administering to the mammal a ligand of FXR.

Figure 4A:
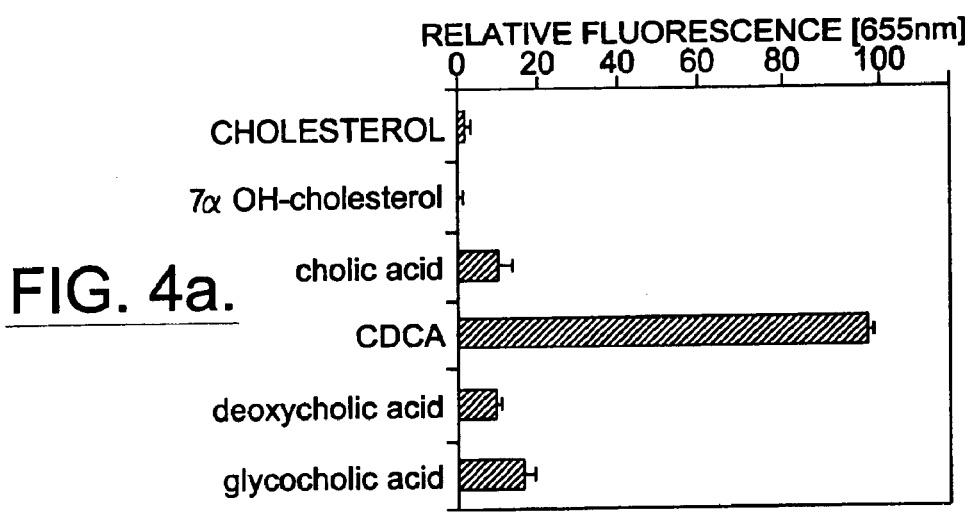
As shown in FIG. 4a, CDCA induced the interaction between FXR and the SRC-1 peptide. Dose response analysis showed that CDCA bound to FXR with an $EC_{50}$ value of ~4.5 μM (FIG. 4b), which is well within the range of the intestinal concentration of this bile acid. Importantly, the closely related bile acids cholic acid and deoxycholic acid had no effect in the FXR FRET assay, demonstrating the specificity of CDCA binding to FXR (FIG. 4a).
Figure 4B:
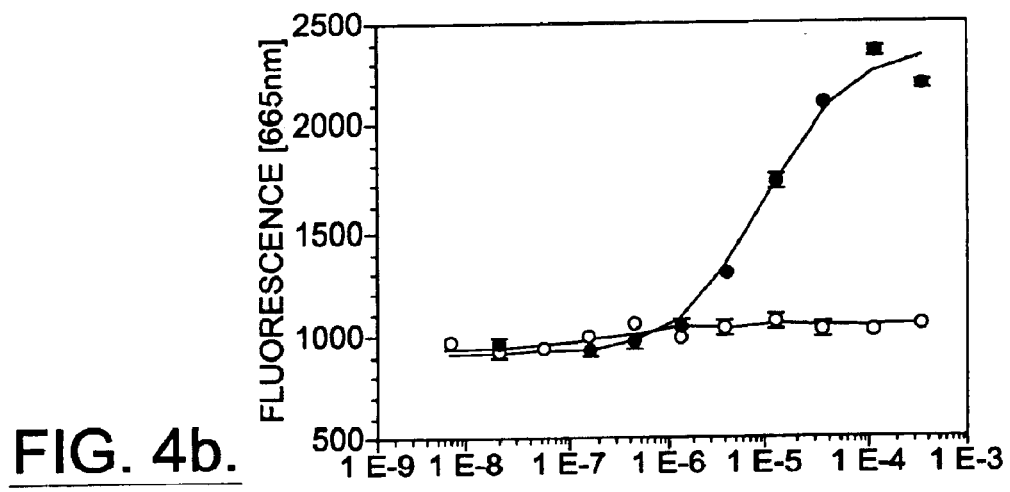
FIG. 4.
Figure 4C:
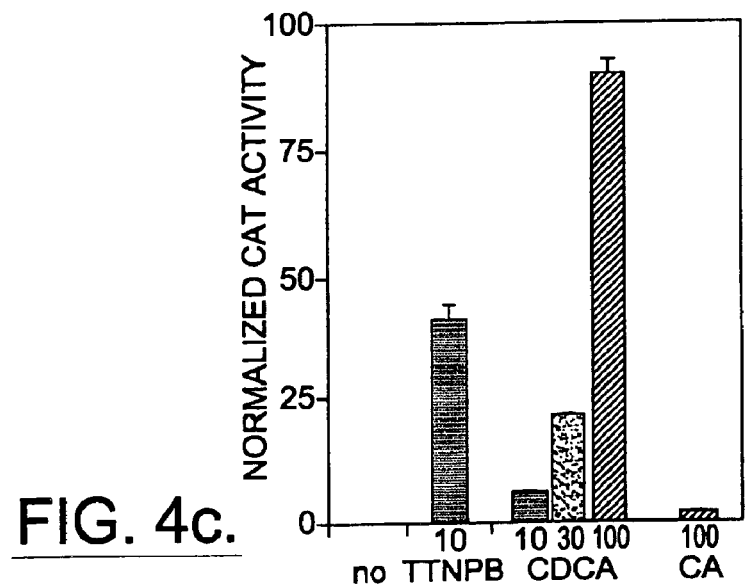

Next examined was whether CDCA activated FXR in cells. CV-1 cells were transiently transfected with an expression plasmid encoding the human FXR and a reporter construct containing the hsp27-EcRE, a response element that is known to be activated by the FXR/RXR heterodimer. A 130-fold activation of the FXR/RXR heterodimer could be achieved with 100 μM CDCA (FIG. 4c).

Figure 5:
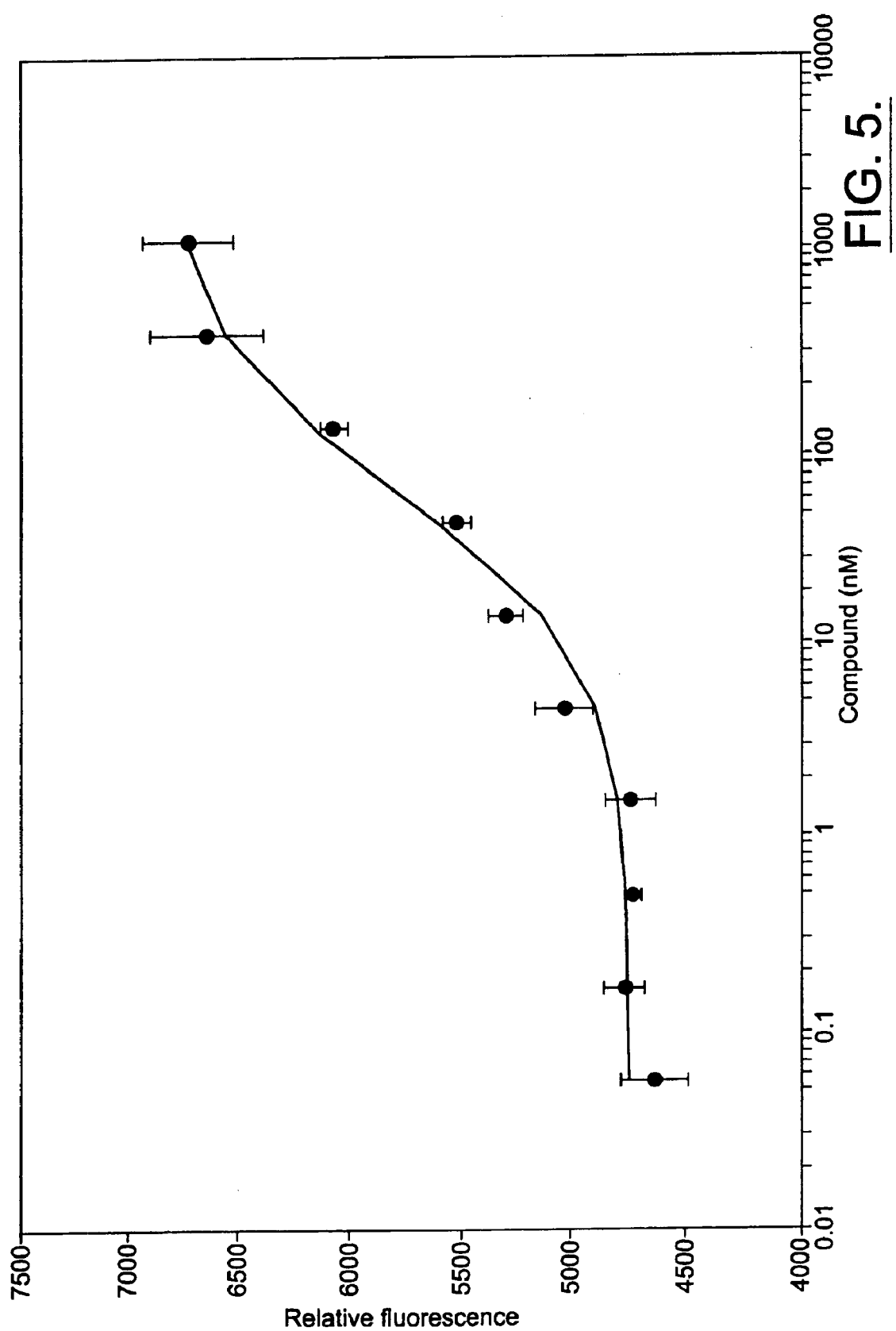

FIG. 5. shows ligand binding to FXR measured by modulation of FXR:RXR heterodimer formation.

DETAILED DESCRIPTION OF THE INVENTION

The present invention includes a generic approach to assay development for nuclear receptors, utilizing purified ligand binding domains. The concept of generic assay development has been extended to develop in vitro assays that detect ligand binding by monitoring ligand induced changes in receptor heterodimerization. This approach has been demonstrated using both scintillation proximity and homogenous time-resolved fluorimetry (HTRF) in the accompanying examples but it is not restricted to these methods. Other marking and measuring techniques may also be used. However, the use of scintillation proximity or HTRF provides a simpler and more practical methodology.

Another aspect of the invention is a nuclear receptor-peptide assay for identifying ligands. This assay utilizes fluorescence resonance energy transfer (FRET) and can be used to test whether putative ligands bind to FXR. The FRET assay is based upon the principle that ligands induce conformational changes in nuclear receptors that facilitate interactions with coactivator proteins required for transcriptional activation.

In FRET, a fluorescent donor molecule transfers energy via a non-radiative dipole-dipole interaction to an acceptor molecule (which is usually a fluorescent molecule). FRET is a standard spectroscopic technique for measuring distances in the 10–70 Å range. Upon energy transfer, which depends on the $R^{-6}$ distance between the donor and acceptor, the donor's fluorescence is reduced, and the acceptor fluorescence is increased, or sensitized. FRET is frequently used in both polymer science and structural biology and has recently been used to study macromolecular complexes of DNA, RNA, and proteins. In addition, Mathis has used europium cryptates with the multichromophoric Allophycocanin to achieve an extremely large $R_0$ of 90 Å (29).

The present invention utilizes the above discussed assays for the discovery of ligands for FXR. Specifically, for example, the invention provides the discovery that CDCA binds and activates the farnasoid X receptor (FXR), an orphan member of the steroid hormone receptor superfamily which is . activated by various farnesol metabolites and the synthetic retinoid TTNPB in cell-based assays. The invention additionally provides that a compound characterized by the following formula (I) is a ligand of FXR:

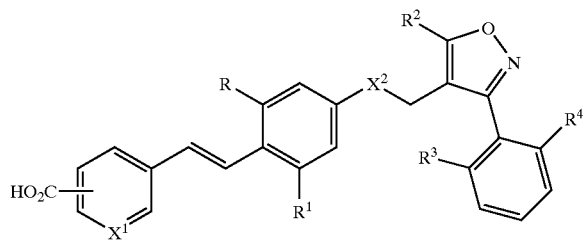

wherein $X^1$ is CH or N; $X^2$ is O or NH; R and $R^1$ may independently be H, lower alkyl, halogen, or $CF_3$; $R^2$ is lower alkyl; $R^3$ and $R^4$ may independently be H, lower alkyl, halogen, $CF_3$, OH, O-alkyl, or O-polyhaloalkyl.

An example of such a ligand is GW4064, a potent and selective FXR ligand, characterized by the following formula (II):

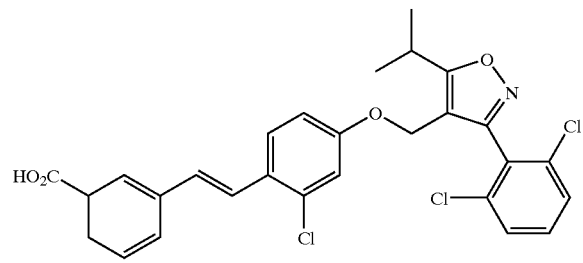

Thus the present invention provides a method of regulating bile acid, cholesterol, and lipid homeostasis using a compound, such as bile acid (particularly CDCA) or a synthetic compound, such as GW4064, that binds the FXR nuclear receptor.

Binding of the FXR nuclear receptor can result in the alteration of expression of various genes that FXR aids in regulating, including genes involved in lipid absorption and digestion in the small intestine and lipid homeostasis in the liver. Examples of such genes can include, but are not limited to, genes involved in bile acid transport, lipid absorption, cholesterol biosynthesis, proteolysis, amino acid metabolism, glucose biosynthesis, protein translation, electron transport, and hepatic fatty acid metabolism. It is noted that FXR often functions as a heterodimer with the Retinoid X Receptor (the FXR/RXR heterodimer). The inventive method includes using this technology to affect bile acid and cholesterol homeostasis such that, ultimately, cholesterol and lipid levels can be modified and in treating diseases in a mammal, including man, in which regulation of bile acid, cholesterol and lipid levels is important.

Thus the present invention provides a method of modulating a gene whose expression is regulated by FXR in a mammal comprising administering to the mammal a ligand of FXR: (a) Genes Downregulated in Liver, such as apolipoprotein B −2.7, plasma proteinase inhibitor alpha-1-inhibitor III group 3 (m22360) −2.7, L-gulono-gamma-lactone oxidase (d12754) −2.2, Peroxisomal enoyl- CoA:hydrotase-3-hydroxyacyl-CoA bifunctional enzyme (k03249) −2.0, liver fatty acid binding protein (L-FABP, m13501) −2.0, CYP4A2 (m57719) −1.9, CYP3A23 (x96721) −1.8

CYP3A1 (x64401) −1.6; (b) Genes Upregulated in Liver, such as small heterodimer partner homolog (d86580) +6.6, insulin-induced growth-response protein, CL-6 (I13619) +5.9, elongation factor 2, EF-2 (y07504) +4.3, mouse cornichon +4.0, protein kinase C receptor (u03390) +3.1, mitochondrial cytochrome c oxidase (m27315) +2.7, cystathione gamma-lyase (x53460, d17370) +2.3, cytosolic phosphoenolpyruvate carboxykinase (k03243) +2.1, histidase (m58308) +2.1, S-adenosylmethionine synthetase (x60822) +2.0, lanosterol 14-alpha-demthylase (u17697)+ 1.9, G protein-coupled purinoceptor P2U (I46865) +1.9, hepatic squalene synthetase (m95591) +1.5; (c) genes having altered expression in intestine: lipase (x61925) −9.5, pancreatic lipase (d88534) −4.4, colipase (m58370) −10.2, pancreatic phospholipase A-2 (d00036) −7.4, pancreatic amylase (m24962) −8.1, carboxypeptidase A1 (m23986) −6.1, carboxypeptidase A2 (m23721) −5.4, carboxypeptidase B (m23959) −4.2, pancreatic trypsin I (j00778) −6.8, pancreatic cationic trypsinogen (m16624), pancreatic trypsinogen II (v01274) −3.6, elastase I (v01234, I00112) −2.3, elastase II (I00118,I00124) −4.6, I-BABP (I22788) +2.3, intestinal fatty acid binding protein (FABP, k01180) −1.8, hepatic squalene synthetase (m95591) +1.9, protein kinase C receptor (u03390) +1.6, elongation factor 2, EF-2 (y07504) +2.4, Small heterodimer partner homolog (d86580) +2.2. Additional genes can be determined by the methods taught herein.

By modulation can be meant upregulation or downregulation, alteration in timing of expression or other means of modulation as known in the art. Modulation of these genes can be used to effect treatments of a variety of diseases and disorders, particularly those discussed herein.

In addition, it has been also found that CDCA, lithocholic acid (LCA), and dexoycholic acid, (DCA) and their conjugated derivatives bind to FXR at concentrations consistent with those found in tissues and known to regulate gene transcription. These bile acids are highly efficacious activators of FXR in cell-based reporter assays. With the conjugated forms of the bile acids, activation is only observed in cells that express a bile acid transporter. Thus, the conjugated derivatives, which account for ~98% of all bile acids in human bile, are likely to represent natural FXR ligands in tissues which express bile acid transporters whereas the unconjugated forms may function as ligands in tissues that do not express these transport proteins.

As can be seen from the examples below, including the studies regarding genes which expression is altered by FXR functioning, the present method can be used in a variety of treatments, including the use of FXR agonists to block fatty acid absorption in the intestine for the treatment of dyslipidemia (reduction of triglycerides, free fatty acids), obesity, and associated diseases (atherosclerosis); the use of FXR agonists to block protein and carbohydrate digestion in the intestine for the treatment of obesity; the use of FXR antagonists to block de novo cholesterol biosynthesis in the liver for the treatment of diseases related to elevated cholesterol levels, including atherosclerosis and gall stones; the use of FXR antagonists to block induction of SHP-1 expression (and consequent repression of CYP7A) for the treatment of diseases related to elevated cholesterol levels, including atherosclerosis and gall stones; the use of SHP-1 antagonists to block SHP-1-mediated repression of CYP7A for the treatment of diseases related to elevated cholesterol levels, including atherosclerosis and gall stones. Since FXR binds to DNA as an obligate heterodimer with RXR, the use of RXR-selective compounds (agonists or antagonists) can be made to effect any of the aforementioned effects via the FXR/RXR heterodimer.

In the assay of the present invention a method is provided for the rapid and simple determination of a ligand for a nuclear receptor which comprises contacting a component to be tested with an isolated nuclear receptor ligand binding domain which may be associated with a marking component, and a dimerization partner for the nuclear receptor ligand binding domain which is also associated with a marker; and measuring the interaction between the marking components to determine whether the component to be tested modifies heterodimerization. Various known markers may be used in the process of the present invention such as radioactive markers. The marker could also be a fluorescent dye. When the marker is radioactive, scintillation proximity may be used to measure the marker. A suitable radioactive marker would be radiolabelled GW4064 or derivative of formula (I). When the marker used is a fluorescent dye, homogenous time-resolved fluorimetry may be used to detect the marker. Other known marking and measuring techniques may be used depending on the marker. However, the markers need to be in close proximity to indicate heterodimerization. That is, to indicate that the component to be tested functions as a ligand for the dimerization pair.

RXRs, such as RXRα, RXRβ, and RXRγ, are examples of nuclear receptors that may be used as the dimerization partners in the process of the present invention. RXRα is exemplified in some of the examples. More dimerization partners may be known or later discovered which can readily be utilized in the assay. It is preferable that the dimerization partners and the nuclear receptor ligand binding domains are recombinant proteins and preferably are bacterially expressed.

This method for the rapid determination of a ligand for a nuclear receptor comprises contacting a component to be tested with an isolated nuclear receptor ligand binding domain which is associated with a first marking component, and a heterodimeric partner for the nuclear receptor ligand binding domain associated with a second marking component, and measuring the interaction between the marking components to determine whether the component to be tested modifies hetero-dimerization.

The first marking component may be a radioactive marker and the second marking component (or second marker) may be a SPA bead. The interaction of the markers in this case is determined by scintillation proximity. Alternatively, the first marking component may be a first fluorescent dye emitting at an emitting wavelength which excites the second marking component which may be a second fluorescent dye. The interaction of the markers in this case is determined by homogenous time-resolved fluorimetry.

The interaction of the marking components in either case is measured by comparing a signal produced by a combination of the heterodimeric partner, the isolated nuclear receptor binding domain and the component to be tested with a signal produced by a combination of the heterodimeric partner and the isolated nuclear receptor ligand binding domain in the absence of the component to be tested.

A compound of formula I or II can be detectably labelled by means known in the art. Radiolabelled GW4064 or a radiolabelled derivative of formula (I) can be used in a competition binding assay to detect compounds that directly interact with FXR. Examples of competition binding assays include SPA assays where FXR is bound to an SPA bead in the presence of radiolabelled GW4064. Compounds that directly interact with FXR will displace radiolabelled GW4064 leading to a detectable signal (see Nichols, Anal Biochem. 1998).

EXAMPLE 1

RXRα LBD

Human Retinoid X Receptor alpha Ligand Binding Domains:

RXR-alpha LBD (amino acids 225–462) was expressed in *E. coli* strain BL21 (DE3) as an amino-terminal polyHistidine tagged fusion protein. Expression was under the control of an IPTG inducible T7 promoter. DNA encoding this recombinant protein and a modified histidine tag was subcloned into the expression vector pRSETa (Invitrogen). The sequence used in the construction of RXR-alpha LBD was derived from Genbank accession number X52773.

Ten-liter fermentation batches were grown in Rich $PO_4$ media with 0.1 mg/mL Ampicillin at 25° C. for 12 hours, cooled to 9° C. and held at that temperature for 36 hours to a density of $OD_{600}$=14. At this cell density, 0.25 mM IPTG was added and induction proceeded for 24 hours at 9° C., to a final $OD_{600}$=16. Cells were harvested by centrifugation (20 minutes, 3500 g, 4° C.), and concentrated cell slurries were stored in PBS at –8° C.

Protein Purification

Routinely, 40–50 g frozen cell paste (equivalent to 2–3 liters of the fermentation batch) was thawed and resuspended in 300 mL TBS, pH 7.2, (25 mM Tris, 150 mM NaCl). Cells were lysed by three passages through a homogenizer (Rannie) and cell debris was removed by centrifugation (30 minutes, 20,000 g, 4° C.). The cleared supernatant was filtered through coarse pre-filters and TBS, pH 7.2, containing 500 mM Imidazole was added to obtain a final imidazole concentration of 50 mM. This lysate was loaded onto a column (3×8 cm) packed with Sepharose [$Ni^{++}$ charged] Chelation resin (Pharmacia) and pre-equilibrated with TBS, pH 7.2, containing 50 mM imidazole. After washing to baseline absorbance, the column was developed with a linear gradient of 50 to 500 mM imidazole in TBS, pH 7.2. Column fractions were pooled and dialyzed against TBS, pH 7.2, containing 5 mM DTT and 0.5 mM EDTA. After dialysis the sample was concentrated using Centriprep 10K (Amicon) and subjected to size exclusion with a column (3×90 cm) packed with Sepharose S-75 resin (Pharmacia) pre-equilibrated with the same buffer.

Biotinylation of Human Retinoid-X Receptor Ligand Binding Domain

Purified RXRα LBD biotinylation was carried out in a manner similar to that described for FXR LBD in example 2.

Labeling of RXRα with CY5™

Purified RXRα LBD was diluted to approximately 10 μM in PBS and approximately five-fold molar excess of Cy5™ monofunctional reactive dye [NHS ester] (Amersham Life Sciences) was added in a minimal volume of PBS. This solution was incubated in the dark with mixing for 30 minutes at ambient room temperature (approximately 23° C.). The modification reaction was stopped by the addition of an excess of Tris-HCl, pH 8. Fluorescent dye modified RXRα LBD was dialyzed at 4° C., with minimal exposure to light, against 4 buffer changes, each of at least 50 volumes, PBS containing 5 mM DTT, 2 mM EDTA, and 2% (w/v) sucrose. Aliquots were frozen on dry ice and stored at –80° C.

EXAMPLE 2

Determination of Ligand Binding to Farnasoid X Receptor: Retinoid X Receptor Heterodimer utilizing Time Resolved Fluorimetry.

This example describes the use of ligand mediated heterodimerization to quantify ligand binding to the nuclear receptor Farnasoid X Receptor (FXR).

The method measures the ability of putative ligands to mediate the heterodimerization between the purified bacterial expressed FXR and RXRα ligand binding domains (LBD). Detection of the associated LBD's are measured by time resolved fluorimetry (TRF). The purified LBD of FXR is labeled with biotin then mixed with stoichiometric amounts of europium labeled streptavidin (Wallac Inc). The purified LBD of RXRα is labeled with CY5™ Equimolar amounts of each modified LBD are mixed together and allowed to equilibrate for at least 1 hour prior to the addition to either variable or constant concentrations of the sample for which the affinity is to be determined. After equilibration, the time-resolved fluorescent signal is quantitated using a fluorescent plate reader. The affinity of the test compound is estimated from a plot of fluorescence versus concentration of test compound added.

A basal level of FXR:RXRα heterodimer formation is observed in the absence of added ligand. Ligands that promote heterodimer formation induce a concentration-dependent increase in time-resolved fluorescent signal. Compounds which bind equally well to both monomeric FXR and to the FXR:RXRα heterodimer would be expected to give no change in signal whereas ligands which bind preferentially to the monomeric receptor would be expected to induce a concentration-dependent decrease in the observed signal.

Methods & Materials

Advance Preparation:

Human Farnasoid X Receptor alpha Ligand Binding Domain

Human FRXα Ligand Binding Domain (FXRα LBD) was expressed in *E.coli* strain BL21 (DE3) as an amino-terminal polyhistidine tagged fusion protein. Expression was under the control of an IPTG inducible T7 promoter. DNA encoding this recombinant protein was subcloned into the pRSET-A expression vector (Invitrogen). The coding sequence of Human FRXα LBD was derived from Genbank accession number U 68233 (amino acids 222 to 472).

Ten-liter fermentation batches were grown in Rich $PO_4$ media with 0.1 mg/mL Ampicillin at 25° C. for 12 hours, cooled to 9° C. and held at that temperature for 36 hours to a density of $OD_{600}$=14. At this cell density, 0.25 mM IPTG was added and induction proceeded for 24 hours at 9° C., to a final$OD_{600}$=16. Cells were harvested by centrifugation (20 minutes, 3500 g, 4° C.), and concentrated cell slurries were stored in PBS at –8° C.

Purification of Receptor Ligand Binding Domain

Routinely, 30–40 g cell paste (equivalent to 2–3 liters of the fermentation batch) was resuspended in 200–250 mL TBS, pH 7.2 (25 mM Tris, 150 mM NaCl). Cells were lysed by passing 3 times through a French Press and cell debris was removed by centrifugation (30 minutes, 20,000 g, 4° C.). The cleared supernatant was filtered through course pre-filters, and TBS, pH 7.2, containing 500 mM imidazole was added to obtain a final imidazole concentration of 50 mM. This lysate was loaded onto a column (6×8 cm) packed with Sepharose [$Ni^{++}$ charged] Chelation resin (Pharmacia) and pre-equilibrated with TBS pH 7.2/50 mM imidazole. After washing to baseline absorbance with equilibration buffer, the column was washed with one column volume of TBS pH 7.2 containing 90 mM imidazole. FXRαLBD was eluted directly with 365 mM imidazole. Column fractions were pooled and dialyzed against TBS, pH 7.2, containing 0.5 mM EDTA and 5 mM DTT. The dialyzed protein sample was concentrated using Centri-prep 10 K (Amicon) and subjected to size exclusion, using a column (3×90 cm) packed with Sepharose S-75 resin (Pharmacia) pre-equilibrated with TBS, pH 7.2, containing 0.5 mM EDTA and 5 mM DTT.

Biotinylation of FXR

Purified FXRα LBD was desalted/buffer exchanged using PD-10 gel filtration columns into PBS [100 mM NaPhosphate, pH 7.2, 150 mM NaCl]. FRXα LBD was diluted to approximately 10 μM in PBS and five-fold molar excess of NHS-LC-Biotin (Pierce) was added in a minimal volume of PBS. This solution was incubated with gentle mixing for 30 minutes at room temperature. The biotinylation modification reaction was stopped by the addition of 2000× molar excess of Tris-HCl, pH 8. The modified FRXα LBD was dialyzed against 4 buffer changes, each of at least 50 volumes, PBS containing 5 mM DTT, 2 mM EDTA and 2% sucrose. The biotinylated FXRα LBD was subjected to mass spectrometric analysis to reveal the extent of modification by the biotinylation reagent. In general, approximately 95% of the protein had at least a single site of biotinylation; and the overall extent of biotinylation followed a normal distribution of multiple sites, ranging from one to nine.

RXRα LBD

RXRα LBD was prepared and labeled with CY5™ in accordance with the procedures set forth in example 1.

Preparation of CY5™-RXR:Streptavidin-(Europium Chelate)-FXR Complex

Equimolar concentrations of biotinylated FXR and streptavidin-conjugated europium chelate were incubated in assay buffer containing 10 mM DTT for at least 10 minutes. To this solution an equimolar concentrations of Cy5™ labeled RXRα was added and allowed to equilibrate for at least 30 min. The premixed receptor was then added in a one-step addition to the compound plate, utilizing e.g., a Titertek Multidrop 384.

Materials:

Assay Buffer: 50 mM KCl, 0. 1 mg/mL BSA, 10 mM DTT, and 50 mM Tris (pH 8) The stock buffer is made by dissolving 2.853 g Tris base, 4.167 g Tris hydrochloride, 3.73 g KCl, and 0. 1 g fatty acid free bovine serum albumin, in 1 L of deionized water. The pH is checked and adjusted to 8.0, if necessary, before adjusting to final volume. 0.154 g of solid DTT is added per 100 mL of buffer just before the start of an experiment.

BSA, fatty acid free
DTT
KCl
Europium labeled Streptavidin: (Wallac CR28-1 00)
Tris Hydrochloride
96 well plates: polypropylene for intermediate dilutions (Costar #3794) and either a clear-bottomed white SPA plates (Costar #3632) or a black Polyfiltronics plate (UP350 PSB) for assays.

Methods:

Experimental Details:

Each well to be assayed contained a previously prepared solution of CY5™ RXRα and Europium labeled FXR and the desired concentration of test samples or controls (100 μL total volume). In general, the total volume was held constant by varying the concentration and volume of premixed receptors to compensate for any changes in the volume of a particular set of samples. The plates were incubated for at least 2 hours at room temperature and the fluorescent signal determined in a Wallac Victor Multilabel Fluorescence Reader.

Data Reduction:

For single concentration assays, the results of each test well were expressed as % of control, C, calculated according to eq. 1.

$$C = 100 * \frac{F_{sample} - F_{basal}}{F_{std} - F_{basal}} \qquad (1)$$

where $F_{sample}$ is the signal observed in a particular sample well, $F_{total}$ is the signal observed in the presence of control inhibitor and $F_{basal}$ is the count rate observed in the presence of no ligand. The values used for $F_{Std}$ and $F_{basal}$ were averages of the corresponding control wells included on every plate.

For Dose response assays, the data were first normalized to % of control using eq. (1). A plot of $C_L$, the % of control observed at ligand concentration L, versus ligand concentration, L was constructed. The data were fit to equation (2) to obtain best-fit parameters for the $EC_{50}$, $F_{max}$ and $F_{basal}$.

$$C_L = F_{basal} + \frac{F_{max} * L}{EC_{50} + L} \qquad (2)$$

Note that $F_{max}$, the maximal amplitude observed at saturating ligand concentrations, can be either a positive or negative value. The sign of this parameter indicates whether a particular test compound favors binding to the FXR:RXR complex (positive $F_{max}$) or to either of the component receptors in a non-heterodimeric state (negative $F_{max}$). Furthermore, both $F_{max}$ and $F_{basal}$ are expressed in units of % of a standard compound.

Results

Both the magnitude and sign of Fmax (the maximal ligand-induced amplitude) must be considered. Note that the definition of the maximal response observed for CDCA= 100% is an arbitrary assignment. The purpose of the normalization is only to allow comparison of values obtained for different compounds on different days and/or using different fluorescence plate readers. The results are shown in FIG. 5.

EXAMPLE 3

FXR is abundantly expressed in liver, intestine, kidney, and adrenal, tissues through which there is significant bile acid flux. Based upon these observations and the FRET and transactivation data, the FXR represents a novel hormone signaling pathway and a transcription factor that induces the expression of I-BABP by CDCA. Thus, identification of ligands that bind to FXR provides a method of effecting some of the therapeutic effects of CDCA through the regulation of bile acid flux, including desaturation of bile, inhibition of intestinal cholesterol absorption, and reduction in triglycerides.

In principle, the biology behind this method is to cause more bile acid to be transported through the gut of a mammal, including man. Thus, the FXR receptor is a target for compounds (such as bile acid or other discovered ligands) that bind it and regulate bile acid transport.

Methods related to inhibiting binding of ligands, such as bile acid and GW4064, to FXR and to activating/inhibiting expression of intestinal bile acid-binding protein (I-BABP, which protein is activated by binding to bile acid-FXR-RXR and is involved in transport of bile acid across membranes in the intestine) are included. Furthermore, increasing the transport of bile acids; stimulating the body to convert cholesterol into bile acid; reducing levels of cholesterol; inhibiting the intestinal absorption of cholesterol; reducing the levels of triglycerides; and treating diseases such as atherosclerosis, gallstone disease, lipid storage disorders are also included.

FXR is a Nuclear Receptor for Chenodeoxycholic Acid

As noted supra, recently a cytosolic binding protein termed intestinal bile acid-binding protein (I-BABP) or fatty acid binding protein 6 (FABP6) was identified as a component of the bile acid transport system in the ileal enterocyte. Kanda et al. showed that expression of I-BABP is dramatically induced by human bile, with chenodeoxycholic acid (CDCA) showing a significantly greater induction effect than other more hydrophilic bile acids. On the basis of this structural activity, Kanda proposed that an unidentified nuclear receptor for CDCA was a transcriptional regulator of the expression of I-BABP in the intestine. It has now been discovered that CDCA binds and activates FXR, an orphan member of the steroid hormone receptor superfamily.

Figure 1:
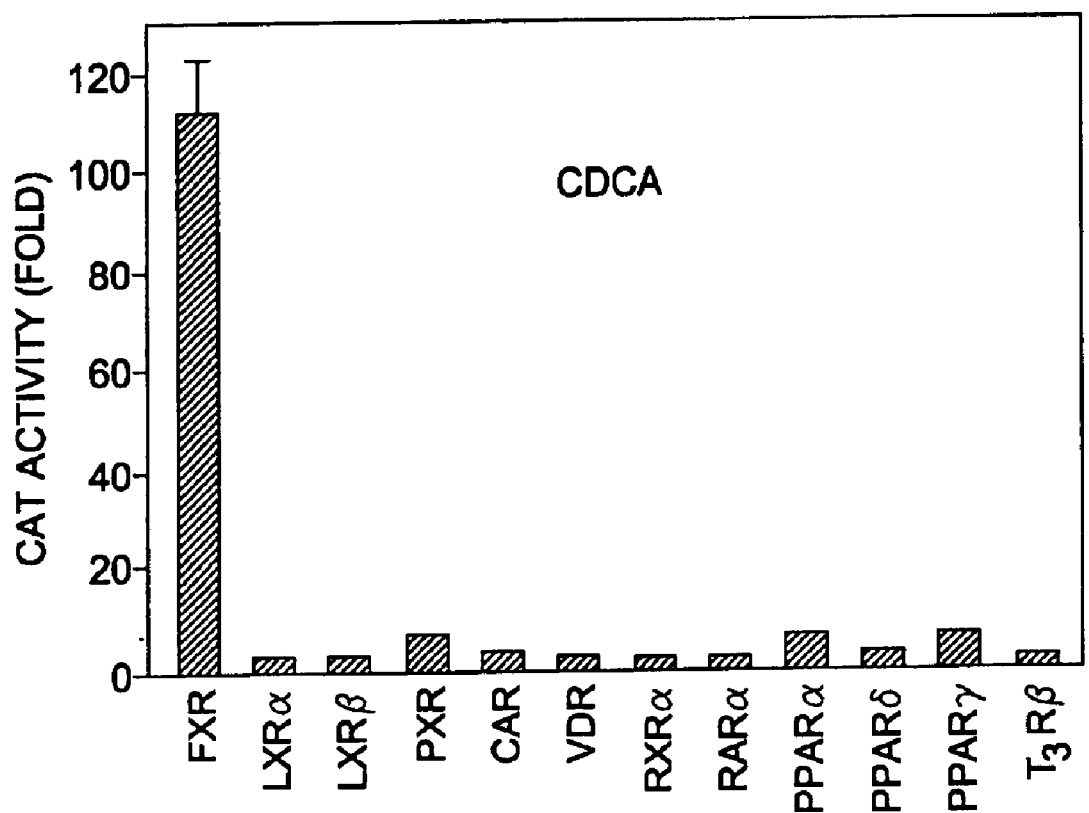
FIG. 1. Shows CDCA selectively activates FXR as compared to other receptors. CV-1 cells were cotransfected with various nuclear receptor-GAL4 chimeras (25) and the reporter plasmid (UAS)$_5$-tk-CAT (26). Cells were treated with 100 µM CDCA. Cell extracts were subsequently assayed for CAT activity (26). Data are expressed for each receptor as fold induction of CAT activity relative to vehicle-treated cells and represent the mean of three data points±SD.

To examine whether CDCA mediated its transcriptional effects through an orphan member of the steroid/retinoid/thyroid hormone receptor family (4) a chimeric receptor system in which the putative ligand binding domain (LBD) of the human orphan receptor is fused to the DNA-binding domain of the yeast transcription factor GAL4 was used. Expression plasmids for the human nuclear receptor-GAL4 chimeras were generated by amplification of the cDNA encoding the putative LBDs and insertion into a modified pSG5 expression vector (Stratagene) containing the GAL4 DNA binding domain (amino acids 1 to 147) and the SV40 Tag nuclear localization signal (5). In CV-1 cells, CDCA selectively activated FXR [NR1H4] (FIG. 1), an orphan nuclear receptor expressed predominantly in the liver, kidney, intestine, and adrenals (7, 8). This strong activation by CDCA was unanticipated because FXR responds to high concentrations of farnesoids (7) and retinoids (9).

Figure 2A:
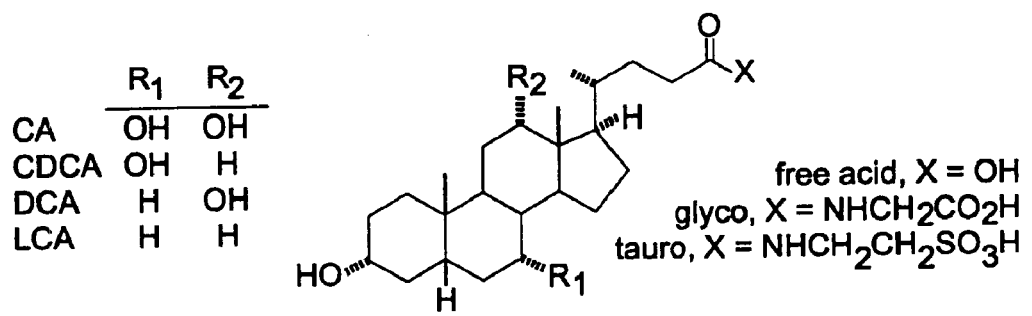
FIG. 2. Shows activation of FXR by bile acids. (A) Chemical structures of major human bile acids. (B) Full-length human (filled bars) and full-length murine (open bars) FXR are activated by CDCA, LCA, and DCA. CAT assays were performed with extracts of CV-1 cells transfected with expression plasmids for human or murine FXR, human RXRα, and the FXREhsp27-tk-CAT reporter plasmid (27, 28). Cells were treated with 100 µM of the indicated bile acid or farnesol, or 10 µM of the indicated steroid or TTNPB. Cholesterol (CH). (C t E) Dose response analysis of bile acids on human FXR. The assays were run as above with 1, 3.3, 10, 33, or 100 µM of CDCA, LCA, or DCA. (F) Human FXR is not activated by CDCA conjugates in CV-1 cells. The assay was run as above with 100 µM free or conjugated CDCA. (G) Human FXR is activated by conjugated bile acids in CV-1 cells expressing the human IBAT gene. The assay was run as above except cells were additionally transfected with an expression plasmid for the human IBAT gene (pCMV-HISBT) and treated with 3 µM of the indicated bile acid. Data are expressed as fold induction of CAT activity relative to vehicle-treated cells and represent the mean of three data points±SD (26).
Figure 2B:
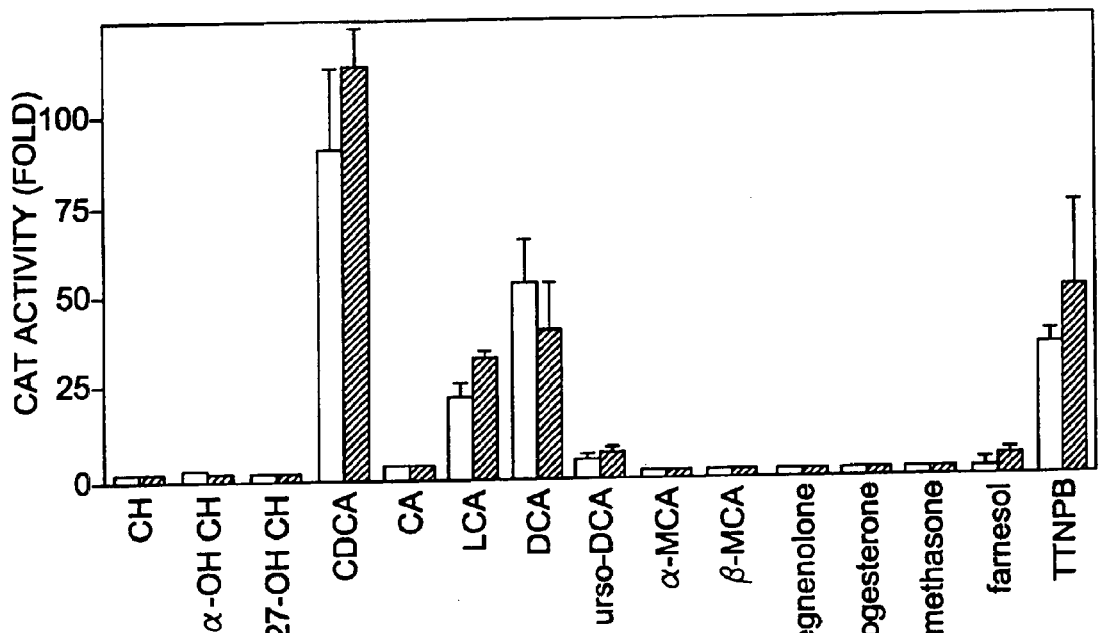
Figure 2C:
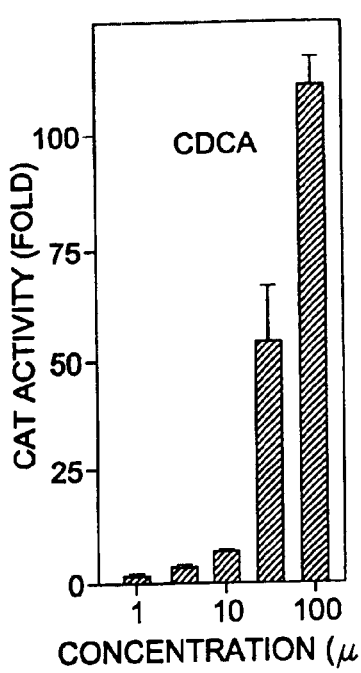
Figure 2D:
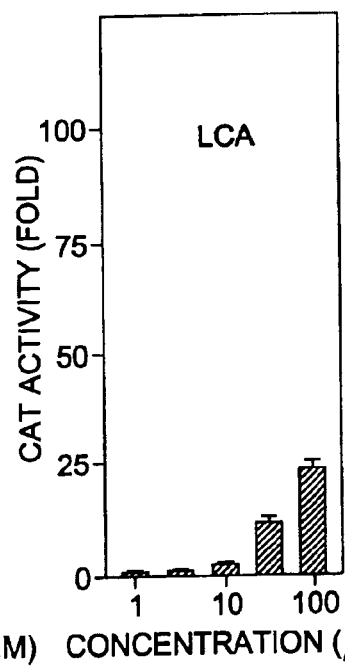
Figure 2E:
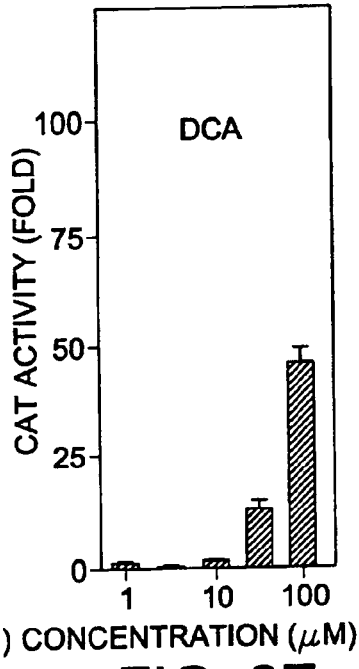
Figure 2F:
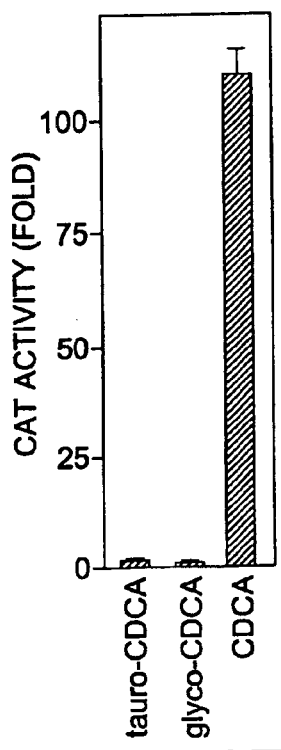

To further investigate the structure-activity relationship of FXR activation, a number of naturally occurring cholesterol metabolites, including bile acids (FIG. 2A), oxysterols and steroids, were tested for their ability to activate full-length human or full-length murine FXR in CV-1 cells. CDCA activated both the human and mouse FXR (FIG. 2B). Dose response analysis showed that although some activation was seen at 3.3 $\mu$M, greater activation was observed at 100 $\mu$M CDCA (FIG. 2C). FXR was also activated by the secondary bile acids lithocholic acid (LCA) and deoxycholic acid (DCA), although these compounds were less efficacious than CDCA (FIGS. 2B to E). A similar activation pattern was observed in various cell lines, including Drosophila-derived S2 cells, indicating that CDCA, LCA, and DCA do not require any specialized metabolic conversion to activate FXR (11). Urso-DCA, the 7$\beta$-hydroxy epimer of CDCA, and cholic acid (CA), which differs from CDCA by only the addition of a hydroxyl group at the 12$\alpha$ position, were inactive on FXR (FIG. 2B). In addition, no activation of FXR was seen with either $\alpha$- or $\beta$-muricholic acid (MCA), the glycine or taurine conjugates of bile acids, oxysterols, farnesol or other products derived from the mevalonate pathway (FIGS. 2B and F). Thus, both the 5$\beta$-cholanoic acid backbone and stereochemistry of the hydroxyl groups in CDCA are critical for optimal FXR activation.

Figure 2G:
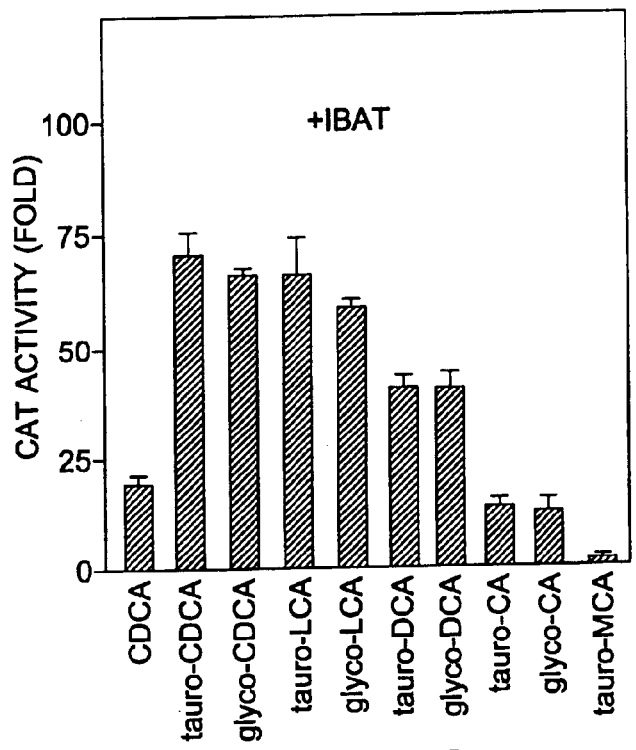

Bile acids are usually found conjugated to glycine or taurine, a derivative of cysteine. Cells require the presence of an active bile acid transporter for uptake of these conjugated derivatives (12). To test whether conjugated bile acids would also activate FXR, the human ileal bile acid transporter (IBAT) was coexpressed with FXR in CV-1 cells (13). FXR was strongly activated by 3 $\mu$M of the taurine or glycine conjugates of CDCA, LCA, and DCA (FIG. 2G). Weaker activation was seen with the conjugated forms of CA and tauro-MCA was inactive (FIG. 2G). These data indicate that FXR can be activated by conjugated bile acids in tissues that express bile acid transporters such as the terminal ileum, liver, and kidney. The relationship between the chemical structure of bile acids and their activation of FXR is in close agreement with the reported effects of bile acids on induction of I-BABP expression in Caco-2 cells and inhibition of CYP7a expression in hepatocytes (3, 12)

EXAMPLE 4

A fluorescence resonance energy transfer (FRET) assay as described further infra, was used to test whether putative ligands bound to a nuclear receptor, FXR. The FRET assay is based upon the principle that ligands induce conformational changes in nuclear receptors that facilitate interactions with nuclear receptor coactivator proteins required for transcriptional activation. The ligand binding domain of FXR labeled with fluorophore allophycocyanin (APC) was incubated with a peptide containing the nuclear receptor interaction domain from the SRC-1 coactivator labeled with europium cryptate.

Both the transactivation and ligand-binding assays typically used to determine activity of putative nuclear receptor activators assess the effect of test ligands on isolated receptor. However, a large proportion of the known orphan nuclear receptors interact with cofactor or coactivator proteins as a complex. Therefore, the present invention suggests the possibility that ligand binding to nuclear receptors may be modulated by the receptor's complexation with a cofactor peptide. The ability of ligand to induce changes in the degree of this complex was then us d as a basis for an inventive assay for the discovery of nuclear receptor ligands. Certain sequences of the cofactor may only be required to interact with the nuclear receptor. Various sequences of the two cofactor proteins SRC-1 and CBP were synthesized and tested in HTRF and Biacore to determine the best sequences to use. The peptide, CPSSHSSLTERHKILHRLLQEGSPS-CONH$_2$ (SEQ ID NO.:1), i.e., SRC-1(LCD2,676-700) was used in screening efforts with FXR and this forms a further aspect of this invention.

Coactivator proteins interact with nuclear receptors in a ligand-dependent manner and augment transcription (9). A short amphipathic $\alpha$-helical domain that includes the amino acid motif LXXLL (SEQ ID NO.:6) (L is Leu and X is any other amino acid) serves as the interaction interface between these coactivator molecules and the ligand-dependent activation function (AF-2) located in the COOH-terminus of the nuclear receptor LBD (10). To test whether ligands would induce a conformation of FXR that favors coactivator binding, a cell-free ligand-sensing assay utilizing fluorescence resonance energy transfer (FRET) to monitor allosteric interaction of a peptide based on the sequence of the steroid receptor coactivator 1 (SRC1) with the receptor was established. The use of FRET to monitor macromolecular complex formation is well established, particularly for immunoassays (11), and this detection methodology has recently been extended to characterize ligand binding to nuclear receptors (12).

Human FXR LBD was prepared and fluorescently labeled as described in Example 2. The LBD of human FXR was labeled with the fluorophore allophycocyanin and incubated with a peptide derived from the second LXXLL (SEQ ID NO.: 6) motif of SRC1 (amino acids 676 to 700) that was labeled with europium chelate. The FRET ligand-sensing assay was performed by incubating 10 nM of the biotinylated FXR LBD that was labeled with streptavidin-conjugated allophycocyanin (Molecular Probes) and 10 nM of the SRC1 peptide [amino acids 676 to 700, 5'-biotin-CPSSHSSLTERHKILHRLLQEGSPS-CONH$_2$] (SynPEP) (SEQ ID NO.:1) that was labeled with streptavidin-conjugated uropium ch late (Wallac), in 50 mM Tris pH 8, 50 mM KCl, 0.1 mg/ml BSA, 1 mM EDTA, and 10 mM DTT, in the presence of test compound for 2 hours at 22° C. Data were collected using a Wallac Victor™ fluorescence reader in a time-resolved mode. The relative fluorescence was measured at 665 nM and the data reduction was as described in Example 1.

Preparation of Streptavidin-(Europium Chelate)-SRC1:Steptavidin-(APC)-FXR Complex Biotinylated SRC-1(LDC2,676-700) peptide and a ½ stoichiometric amount of streptavidin-conjugated europium chelate were incubated in assay buffer containing 10 mM DTT for at least 30 minutes. A second solution of stoichiometric amounts of biotinylated FXR and streptavidin-conjugated APC were incubated in assay buffer containing 10 mM DTT for at least 30 minutes. Each solution was then blocked with a 5 fold molar excess of biotin and allowed to equilibrate for at least 15 minutes. The labeled receptor and labeled peptide were mixed and again allowed to equilibrate for at least 30 minutes, then added in a one-step addition to the compound plate, utilizing, e.g., a Titertek Multidrop 384.

Materials:
APC-labeled streptavidin FXR and Europium labeled streptavidin SRC-1(LDC2,676-700)
SRC-1(LDC2,676-700:(SynPEP)
APC-Labeled streptavidin FXR and Europium labeled streptavidin SRC1(LCD2,676-700)
Biotinylated Human Farnasoid-X receptor LBD:
Biotinylated SRC-1(LDC2,676-700): Biotin-CPSSHSSLTERHKILHRLL-QEGSPS-CONH$_2$ (SynPEP) (SEQ ID NO.:1)

Assay Buffer: 50 mM KCl, 2 mM EDTA, 0.1 mg/mL BSA, 10 mM DTT, and 50 mM Tris (pH 8). The stock buffer is made by dissolving 2.853 g Tris base, 4.167 g Tris hydrochloride, 3.73 g KCl, 0.74 g EDTA (disodium salt, dihydrate) and 0.1 g fatty acid fre bovine serum albumin, in 1 L of deionized water. The pH is checked and adjusted to 8.0, if necessary, before adjusting to final volume. 0.154 g of solid DTT is added per 100 mL of buffer just before the start of an experiment.

BSA, fatty acid free
DTT
EDTA, disodium salt dihydrate
KCl
Allophycocyanin labeled streptavidin: (Molecular Probes S-868)
Europium labeled Streptavidin: (Wallac CR28-100)
Tris Hydrochloride
96 well plates: polypropylene for intermediate dilutions (Costar #3794) and either a clear-bottomed white SPA plates (Costar #3632) or a black Polyfiltronics plate (UP350 PSB) for assays.

Results

Figure 3A:
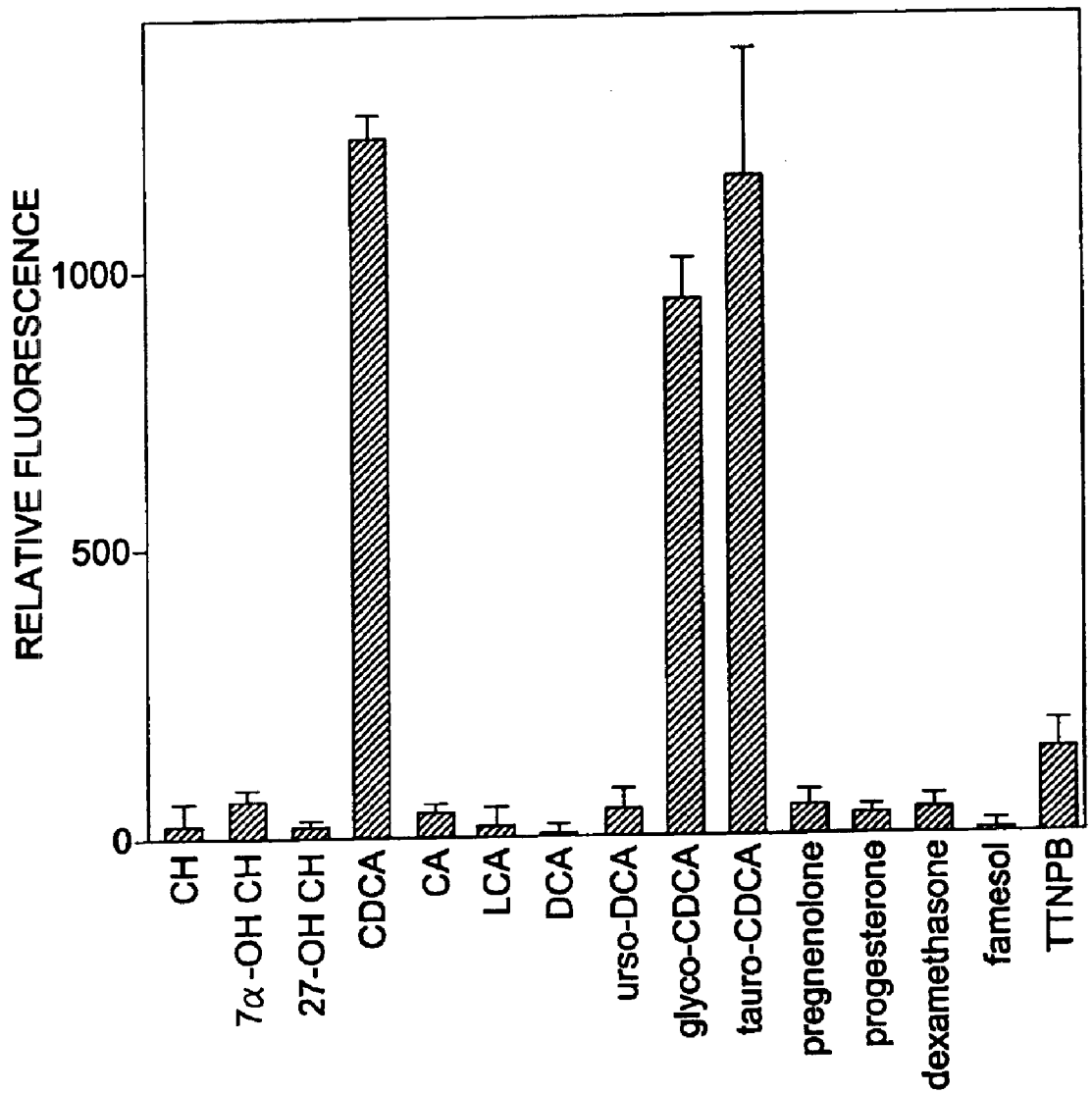
FIG. 3. Shows free and conjugated bile acids bind to FXR. (A) CDCA and its conjugates increase SRC1 binding to FXR. The FRET ligand-sensing assay was run with 10 nM of the biotinylated FXR LBD labeled with streptavidin-conjugated allophycocyanin, 10 nM of a SRC1 peptide labeled with streptavidin-conjugated europium chelate, and 100 μM of the indicated compound. Data are expressed as the means±SD derived from three independent experiments. (B) Dose response analysis of CDCA binding to FXR. The FRET ligand-sensing assay was run in the presence of increasing concentrations of CDCA (open circles), glyco-CDCA (open triangle), tauro-CDCA (open boxes), or cholic acid (closed circles). (C) LCA, DCA, and TTNPB compete with CDCA for FXR binding. FRET ligand-sensing assays were run in the presence of 50 μM CDCA and increasing concentrations of LCA (open circles), DCA (open boxes), and TTNPB (closed circles).

Ligands, in particular CDCA and the corresponding glycine and taurine conjugates, increased the interaction between FXR and the SRC1 peptide as determined with time-resolved FRET (FIG. 3A). Dose response analysis showed that CDCA, glyco-CDCA and tauro-CDCA increased the amount of SRC1 peptide bound to the FXR LBD. A typical saturable concentration response curve characteristic of specific interaction was observed.

TABLE 1

Figure 3B:
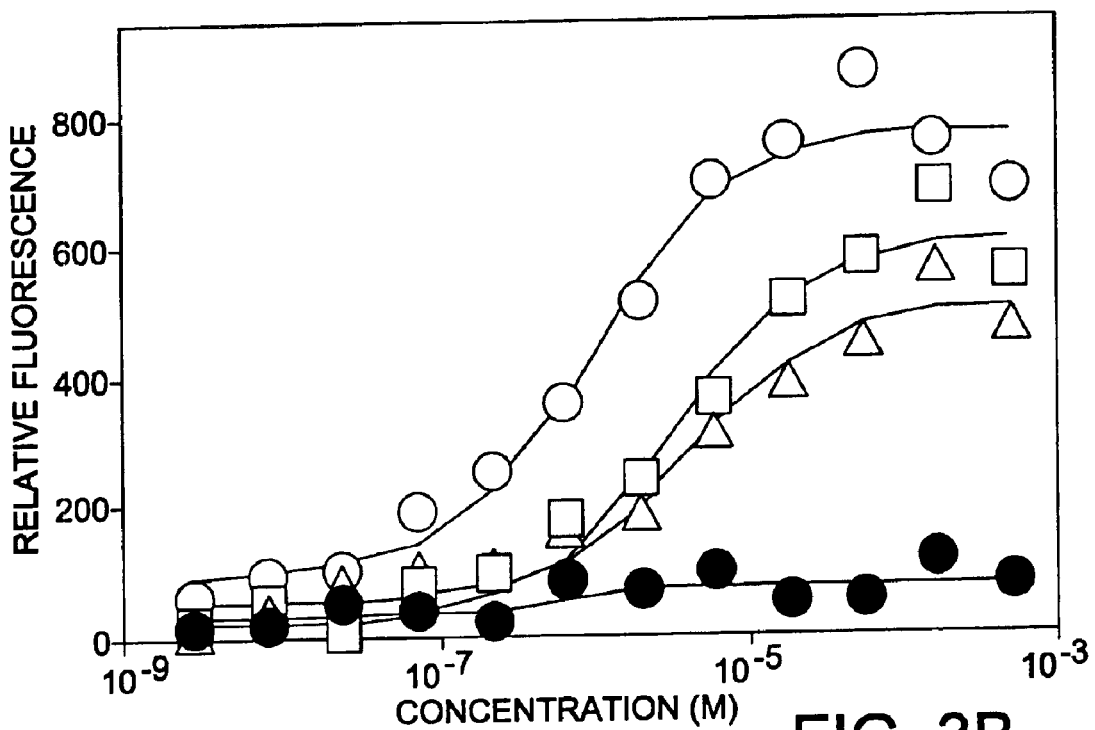

Potency of bile acids for binding to FXR as determined in the cell-free ligand sensing assay. The indicated values for CDCA and its conjugates are EC$_{50}$s derived from dose response analysis as described in FIG 3B. The indicated values for other bile acids and their conjugates are half-maximal inhibitor concentrations IC$_{50}$s derived from dose response analysis as described in FIG. 3C.

| Bile Acid | fre acid | glycin-conjugate | taurine-conjugate |
| --- | --- | --- | --- |
| CDCA | 4.5 µM | 10 µM | 10 µM |
| CA | >1000 µM | >1000 µM | >1000 µM |
| LCA | 3.8 µM | 4.7 µM | 3.8 µM |
| DCA | 100 µM | ≧500 µM | ≧500 µM |
| MCA | >1000 µM | Not tested | ≧500 µM |

Figure 3C:
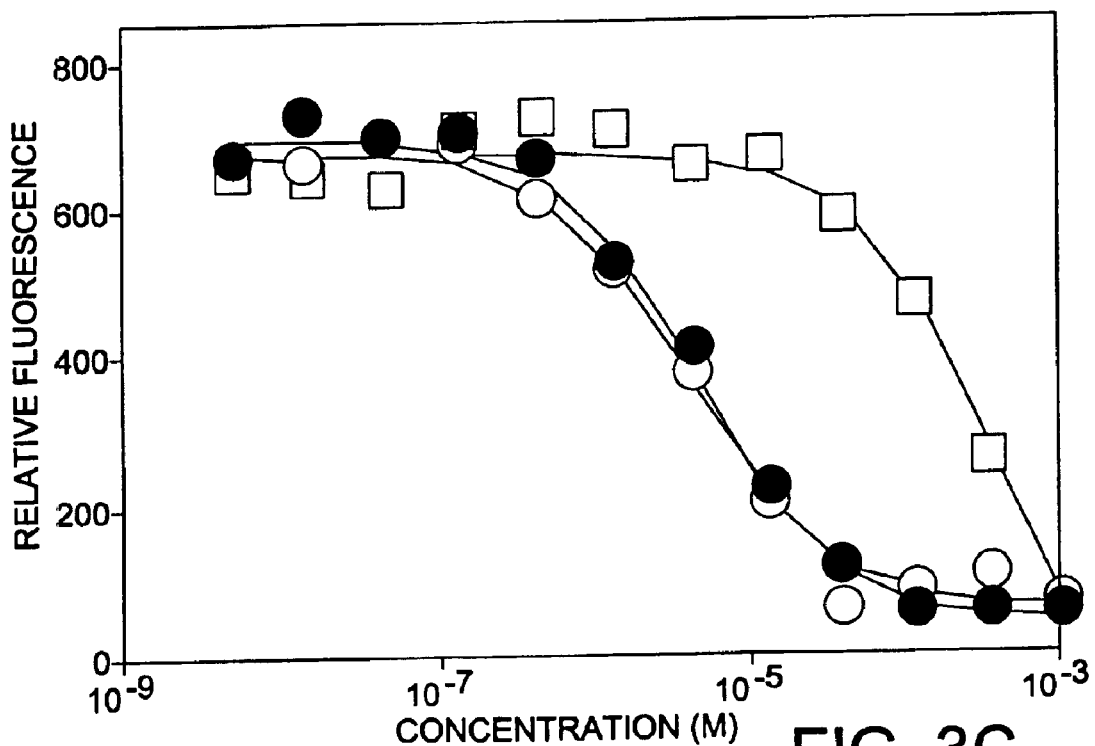

Although LCA, DCA, and (E)-[(tetrahydrotetramethyinaphthalenyl)-propenyl]-benzoic acid (TTNPB) activate FXR in the cell-based reporter assay (FIG. 2B), they did not promote interactions between the FXR LBD and SRC1 in the FRET ligand-sensing assay (FIG. 3A). However, when these compounds were assayed in the presence of 50 µM CDCA, they disrupted the CDCA-FXR-SRC1 complex in a dose-dependent fashion (FIG. 3C and Table 1). Thus, CDCA, LCA, DCA, and TTNPB are ligands for FXR. Similarly, the taurine and glycine conjugates of LCA decreased the fluorescence signal, indicating displacement of CDCA from FXR with IC$_{50}$ values of 3.8 and 4.7 µM, respectively (Table 1). The conjugated forms of DCA and MCA caused a small decrease in fluorescence at the highest concentration tested, and no effect was obtained with the conjugated forms of CA and urso-DCA (Table 1).

As used in the claims for this assay, "nuclear receptor coactivator peptide" means a peptide whose affinity for the receptor is changed in the presence of ligand and which has a LXXLL (SEQ ID NO.:6)motif. Examples of coactivator peptides useful for ligand identification by this method that have been demonstrated to interact with FXR include SRC-1 and those listed below:

1. B-QEQLSPKKKENNALLRYLLDRDDPS-CONH$_2$ (SEQ ID NO.: 2), ACTR (734–758), RAC3 (724–748), SRC-3 (724–748), AIB1 (724–748), pCIP (716–740)
2. B-QEPVSPKKKENALLRYLLDKDDTKD-CONH$_2$ (SEQ ID NO.:3), TIF2 (732–756)
3. B-GSTHGTSLKEKHKILHRLLQDSSSPVD-CONH$_2$ (SEQ ID NO.:4), TIF2 (676–702)
4. B-SNMHGSLLQEKHRILHKLLQNGNSPAE-CONH$_2$ (SEQ ID NO.:5), pCIP (664–690), RAC3 (671–697), ACTR (681–707), AIB1 (671–697)

The sequences of peptides 1 and 4 appear in a number of coactivators, hence the multiple names. The "B" in the s quences stands for biotinylated, which is a modification that allows attachment of the peptide during the analysis.

EXAMPLE 5

The present invention provides the non-steroidal compound GW4064 as a potent and selective FXR ligand.

Synthesis of GW4064

A solution of 2,6-dichlorobenzaldehyde (25 g, 0.14 mole) in ethanol (200 mL) was added to a solution of hydroxylamine hydrochloride (11 g, 0.16 mole) and sodium hydroxide (6.3 g, 0.16 mole) in water (100 mL). The resulting mixture was stirred at 90° C. for 24 hours. The volume was reduced in vacuo by ca 30 mL which induced a precipitate. The flask was then cooled to room temperature and the white solids were collected by filtration and washed with water (2×100 mL). Yield=25.9 g. (96%) of 2,6-dichlorobenzaldehyde oxime. A 500 mL round bottom flask was charged with a solution of 2,6-dichlorobenzaldehyde oxime (13 g, 0.07 mole) in N,N-dimethyl formamide (150 mL). The flask was placed in an ambient temperature water bath. The flask was then charged with N-chlorosuccinimide (9.2 g, 0.07 mole). Within minutes of dissolution, an exotherm was observed along with a significant color change to dark yellow. The reaction was stirred an additional hour then the contents were then poured into water (200 mL) and the product extracted with diethyl ether (300 mL). The ethereal layer was washed with water (3×100 mL) and brine (50 mL), then dried over anhydrous magnesium sulfate. After filtering, the solvent was removed in vacuo to yield 14.5 g of a yellow oil. (94%) of 2,6-dichlorophenyl hydroximic chloride which was used without further purification. A stirred solution of methyl isobutyryl acetate (2 g, 15.6 mmol) in tetrahydrofuran (15 mL) was treated with a solution of sodium methoxide (31.5 mL, 0.5 M in methanol) followed by a solution of 2,6-dichlorophenyl hydroximic chloride (3.5 g, 15.6 mmol) in tetrahydrofuran (5 mL). After stirring at ambient temp 16 h the solvent was removed in vacuo. The resulting residue was partitioned with diethyl ether (100 mL) and water (100 mL). The ethereal layer was washed with brine (50 mL), dried over anhydrous magnesium sulfate, filtered and condensed to an oil. The product was purified by flash chromatography on silica gel using 10% ethyl acetate in hexane as mobile phase. Yield=3.1 g. (62%) of 3-(2,6-dichlorophenyl)-4-carbomethoxy-5-isopropyl-isoxazole.

A solution of 3-(2,6-dichlorophenyl)-4-carbomethoxy-5-isopropyl-isoxazole (8.4 g, 27 mmol) in tetrahydrofuran (60 mL) was cooled to 0° C. under a nitrogen atmosphere while a solution of diisobutylaluminum hydride (38 mL, 1.5M in toluene) was added dropwise. The reaction was allowed to warm slowly to ambient temperature over several hours and stir at room temperature 16 h total. The flask was again cooled to 0° C. and methanol (2 mL) was carefully added over a 10 minute period. Water (20 mL) was added dropwise and a gelatinous mixture formed. Sodium hydroxide (30 mL, 2N) was added and the material was filtered over a plug of celite. After the solids were nearly dry, they were extracted with ethyl acetate (4×50 mL) and the filtrates were combined. The organic layer was washed with water (2×50 mL), brine (50 mL), were dried over anhydrous magnesium sulfate, filtered and condensed to a white crystalline solid. Yield=7.1 g. (93%) of 3-(2,6-dichlorophenyl)-4-hydroxymethyl-5-isopropyl-isoxazole.

A solution of 2-chloro-4-hydroxy-benzaldehyde (0.5 g, 3.2 mmol) and 3-(2,6-dichlorophenyl)-4-hydroxymethyl-5-isopropyl-isoxazole (0.9 g, 3.2 mmol) and triphenylphosphine (0.84 g. 3.2 mmol) in dichloromethane (10 mL) was treated with diisopropyl azodicarboxylate (0.63 mL, 3.2 mmol) dropwise. A brief exotherm was observed and the reaction was stirred at ambient temperature 4 hours. The solvent was removed in vacuo and the resulting residue was purified by flash chromatography on silica gel using dichloromethane as the mobile phase. Yield=0.86 g. (63%) of 3-(2,6-dichlorophenyl)-4-(3'-chloro-4'-formylphenoxy)-methyl-5-isopropyl-isoxazole.

Methyl-3-bromomethyl-benzoate (14 g, 61 mmol) in triethylphosphite (12 mL, 70 mmol) was stirred at 185° C. for 4 hours. Excess triethylphosphite was removed by vacuum distillation (150 mT, 145° C.) and the resulting oil was used without further purification. Yield=17.5 g. (100%) of diethyl (3-methoxycarbonyl) benzyl phosphonate.

A solution of diethyl (3-methoxycarbonyl) benzyl phosphonate (0.68 g, 2.4 mmol) in tetrahydrofuran (5 mL) was treated with sodium hydride (0.1 g, 2.5 mmol 60% dispersion in oil). Vigorous gas evolution was observed. Once the bubbling subsided, 3-(2,6-dichlorophenyl)-4-(3'-chloro-4'-formylphenoxy)-methyl-5-isopropyl-isoxazole (0.85 g, 2 mmol) as a solution in tetrahydrofuran (3 mL) was added dropwise and the reaction was stirred 5 hours at ambient temperature. The volume was diluted to 70 mL with ethyl acetate and the mixture was washed with water (50 mL), saturated sodium bisulfate (20 mL), and brine (50 mL). The organic phase was dried over anhydrous magnesium sulfate, filtered, and condensed to an oil. This material was purified by flash chromatography on silica gel using dichloromethane as the mobile phase. Yield=0.95 g. (86%) of 3-(2,6-dichlorophenyl)-4-(3'-carbomethoxy-2-chlorostilben-4-yl)-oxymethyl-5-isopropyl-isoxazole.

A solution of (6.3 g, 11.3 mmol) in tetrahydrofuran (25 mL) was treated with lithium hydroxide (25 mL, 1M in water) and the mixture was stirred vigorously at room temperature 24 hours. The tetrahydrofuran was removed in vacuo and the resulting residue was partitioned with ethyl acetate (300 mL), water (100 mL), and saturated sodium bisulfate (5 mL). The organic phase was washed with water (50 mL), brine (50 mL) then was dried over anhydrous magnesium sulfate, filtered, and condensed to yield a yellow residue. The product was purified by flash chromatography on silica gel using ethyl acetate as the mobile phase. Yield=6.0 g, (98%) of 3-(2,6-dichlorophenyl)-4-(3'-carboxy-2-chloro-stilben-4-yl)-oxymethyl-5-isopropyl-isoxazole.

GW4064 activates rodent FXR with a half maximal effective concentration ($EC_{50}$) of approximately 300 nM in cell-based reporter assays. Tissues have been examined from vehicle or GW4064-treated rats for genes that are differentially expressed. FXR target genes have been identified in the liver and intestine, two tissues where FXR is abundantly expressed. Our data provide evidence for a broad role for FXR in lipid homeostasis and digestion. Furthermore, our data indicate utilities for FXR ligands in the treatment of diseases associated with impaired/altered lipid homeostasis and digestion.

Fischer rats were treated with either vehicle alone or 30 mg/kg of the FXR-selective ligand GW4064 for 7 days. At the end of the study, serum lipid levels were determined. Serum triglyceride levels were decreased by 26% in GW4064-treated animals. Similarly, natural bile acids, which serve as FXR ligands, lower triglyceride levels when administered to rodents or man (Iser and Sali, 1981). Our data with the non-steroidal FXR ligand GW4064 demonstrate that FXR mediates the triglyceride-lowering effects of bile acids.

Liver and small intestine were removed from GW4064- and vehicle-treated Fischer rats and cDNA prepared. Curagen GeneCall technology was employed to identify genes that were differentially regulated by GW4064 in these tissues.

Intestine

Nearly twenty genes were identified in the intestine that were regulated >1.5-fold by GW4064 (Table 2). The expression of roughly half of these genes was decreased by GW4064 treatment. Notably, all of these downregulated genes are involved in either lipid absorption or proteolysis.

Among the genes involved in lipid absorption are three lipases (lipase, pancreatic lipase, and pancreatic phospholipase A2), a colipase, and the intestinal fatty acid binding protein. The proteases carboxypeptidase A1, carboxypeptidase A2, carboxypeptidase B, pancreatic trypsin I, cationic trysinogen, pancreatic trypsinogen II, elastasel, and elastase II were all down regulated ≧2 fold. Finally, pancreatic amylase, which hydrolyzes starches and glycogen, was downregulated >8-fold. Taken together, these data provide evidence that FXR plays an important role in the coordinate regulation of digestion in the small intestine, including the metabolism of fatty acids, protein, and carbohydrates. Moreover, these data suggest that bile acids, as natural FXR ligands, serve a broader role in the regulation of digestion in the small intestine than was previously appreciated.

Among the genes whose expression was increased by GW4064 in the intestine was the pr viously established FXR target gene IBABP. Expression of hepatic squalene synthetase, an enzyme essential for cholesterol biosynthesis, and the orphan nuclear receptor short heterodimerizing partner 1 (SHP-1) was also increased in the intestine. SHP-1 may be involved in the coordinate down-regulation of genes modulated by nuclear receptors, as discussed below.

TABLE 2

A. Genes Downregulated in Liver

| | |
|---|---|
| apolipoprotein B | −2.7 |
| plasma proteinase inhibitor alpha-1-inhibitor III group 3 (m22360) | −2.7 |
| L-gulono-gamma-lactone oxidase (d12754) | −2.2 |
| Peroxisomal enoyl-CoA:hydrotase-3-hydroxyacyl-CoA bifunctional enzyme (k03249) | −2.0 |
| liver fatty acid binding protein (L-FABP, m13501) | −2.0 |
| CYP4A2 (m57719) | −1.9 |
| CYP3A23 (x96721) | −1.8 |
| CYP3A1 (x64401) | −1.6 |

B. Genes Upregulated in Liver

| | |
|---|---|
| Small heterodimer partner homolog (d86580) | +6.6 |
| insulin-induced growth-response protein, CL-6 (l136-3619) | +5.9 |
| elongation factor 2, EF-2 (y07504) | +4.3 |
| Mouse cornichon | +4.0 |
| protein kinase C receptor (u03390) | +3.1 |
| mitochondrial cytochrome c oxidase (m27315) | +2.7 |
| cystathione gamma-lyase (x53460, d17370) | +2.3 |
| cytosolic phosphoenolpyruvate carboxykinase (k03243) | +2.1 |
| histidase (m58308) | +2.1 |
| S-adenosylmethionine synthetase (x60822) | +2.0 |
| lanosterol 14-alpha-demthylase (u17697) | +1.9 |
| G protein-coupled purinoceptor P2U (l46865) | +1.9 |
| h patic squalene synthetase (m95591) | +1.5 |

Liver

Unlike the intestine, most liver genes whose expression was affected by GW4064 were upregulated (Table 3). Expression of the gene encoding the orphan nuclear receptor SHP-1 was increased the most, nearly 7-fold. SHP-1 was originally cloned in a yeast two hybrid assay based on its interaction with the orphan nuclear receptor CAR (Seol et al., 1996). Unlike most nuclear receptors, SHP-1 lacks a DNA-binding domain. In addition to CAR, SHP-1 interacts with other nuclear receptors including thyroid hormone receptor, retinoic acid receptor, RXR, estrogen receptor α, estrogen receptor β, peroxisome proliferator-activated receptor α, and hepatocte nuclear receptor 4 α. In cell-based reporter assays, SHP-1 specifically inhibits transactivation by the family members with which it interacts (Johansson et al., 1999; Masuda et al., 1997; Seol et al., 1996). Thus, the induction of SHP-1 gene expression by FXR ligands may, in turn, result in decreases in expression of genes regulated by nuclear receptors. This mechanism is likely to have important implications in the regulation of CYP7a gene expression by bile acids (see below).

TABLE 3

Genes Having Altered Expression in Intestine:

| | |
|---|---|
| lipase (x61925) | −9.5 |
| pancreatic lipase (d88534) | −4.4 |
| colipase (m58370) | −10.2 |
| pancreatic phospholipase A-2 (d00036) | −7.4 |
| pancreatic amylase (m24962) | −8.1 |
| carboxypeptidase A1 (m23986) | −6.1 |
| carboxypeptidase A2 (m23721) | −5.4 |
| carboxypeptidase B (m23959) | −4.2 |
| pancreatic trypsin I (j000778) | −6.8 |
| pancreatic cationic trypsinogen (m16624) | |
| pancreatic trypsinogen II (v01274) | −3.6 |
| elastase I (v01234, I00112) | −2.0 |
| elastase II (I00118, I00124) | −4.6 |
| I-BABP (I22788) | +2.3 |
| intestinal fatty acid binding protein (FABP, k01180) | −1.8 |
| hepatic squalene synthetase (m95591) | +1.9 |
| protein kinase C receptor (u03390) | +1.6 |
| elongation factor 2, EF-2 (y07504) | +2.4 |
| Small heterodimer partner homolog (d86580) | +2.2 |

GW4064 treatment induced the expression of two enzymes required for de novo cholesterol biosynthesis, lanosterol 14-alpha demethylase and squalene synthetase.

GW4064 treatment increased the expression of a number of genes whose products have well-established roles in various cellular processes including amino acid metabolism (cystathionase, histidase, S-adenosylmethionine), glucose biosynthesis (phosphoenolpyruvate carboxykinase), protein translation (elongation factor 2), and electron transport (mitochondrial cytochrome c oxidase). GW4064 treatment also increased expression of the activated protein kinase C binding protein RACK1, the P2U ATP receptor, cornichon, and insulin-induced growth-response protein CL-6. The latter gene is interesting in that it is abundantly expressed in proliferating hepatocytes during development and regeneration.

Consistent with the observed down-regulation of genes involved in fatty acid absorption in the intestine, GW4064 treatment decreased expression of genes involved in hepatic fatty acid metabolism, including fatty acid oxidation (peroxisomal bifunctional protein, CYP4A2), transport (liver fatty acid binding protein), and secretion (apolipoprotein B). Thus FXR appears have a coordinate role in the regulation of fatty acid homeostasis in the intestine and liver. GW4064 treatment also decreased expression of genes involved in steroid and xenobiotic metabolism (CYP3A23), vitamin C biosynthesis (L-gulono-gamma-lactone oxidase), and inflammatory response (plasma proteinase inhibitor alpha-1-inhibitor group III).

Results

Our results implicate FXR, and by inference its bile acid ligands, in the coordinate regulation of genes involved in lipid absorption and digestion in the small intestine and lipid homeostasis in the liver. Moreover, our results suggest several mechanisms whereby FXR may regulate CYP7a expression in the liver.

Lipid Absorption and Digestion

Our data indicate that FXR regulates a program of genes involved in digestive processes in the small intestine. Thus, a model for FXR effects in the small intestine has been drawn. The ingestion of dietary fatty acids results in cholecystokinin (CCK) release from specialized endocrine cells in the small intestine. CCK, in turn, effects the release of proteases required for digestion and the contraction of the gall bladder, which releases bile acids into the duodenum. The released bile acids may activate FXR and result in decreases in the expression of lipases, a colipase, and proteases in the small intestine. Thus, FXR may serve as a central regulator in the feedback regulation of digestion, sensing bile acids released during the course of digestion and reducing the expression of genes involved in the digestion and absorption of fatty acids and protein. It is well established that increases in bile acids reduce triglyceride levels in mammals (Iser and Sali, 1981). The present model suggests that these decreases in triglyceride levels are due in part to decreased absorption of fatty acids in the small intestine.

The present data also indicate that FXR has coordinate effects on the regulation of fatty acid metabolism in the liver. Consistent with decreased lipid absorption in the intestine, the expression levels of genes involved in hepatic oxidation, transport (liver fatty acid binding protein), and secretion (apoB) of fatty acids are decreased by an FXR ligand.

Implications of FXR in the Regulation of CYP7a

Two possible mechanisms for bile acid feed back and regulate the expression of CYP7a can thus be drawn. First, expression of the orphan receptor SHP-1 was dramatically increased in the livers of GW4064-treated rats. SHP-1 is known to heterodimerize with and suppress the activity of a number of nuclear receptors, including thyroid hormone receptor and hepatocyte nuclear receptor 4 $\alpha$, both of which have been implicated in the regulation of CYP7a expression (Johansson et al., 1999; Masuda et al., 1997; Seol et al., 1996). The present invention provides that SHP-1 expression was also increased in the small intestine of GW4064-treated rats. FXR-mediated increases in SHP-1 gene expression may account in part for the down-regulation of gene expression that is observed in both the liver and small intestine of GW4064-treated rats. An interesting extension is that compounds that bind to SHP-1 and block its ability to antagonize other nuclear receptors may have therapeutic utility in the up-regulation of CYP7a expression and increased metabolism of cholesterol to bile acids.

GW4064 treatment also resulted in increases in the expression of RACK1, which binds activated protein kinase C. RACK1 is a shuttling protein that moves activated protein kinase C between intracellular sites (Rodriguez et al., 1999). Interestingly, the activation of protein kinase C has been shown to repress CYP7a expression in primary cultures of rat hepatocytes and to inhibit bile flow in the perfused rat liver model (Bouscarel et al., 1999). Thus, FXR-mediated effects on protein kinase C signaling pathways may impact the expression of CYP7a and perhaps other genes.

The compounds of Formula (I) or (II) can be synthesized using standard techniques of organic chemistry. A convergent strategy can be employed in which a hydroxystilbene and a hydroxymethyisoxazole are prepared independently and then condensed using a Mitsunobu coupling to generate the ether linkage. Compounds with anilino linkages can be prepared by converting the hydroxyl residue of a hydroxymethyisoxazole into a leaving group, such as bromide or mesylate, followed by reaction with an aminostilbenes.

Hydroxymethylsoxazoles can be prepared by the condensation of a $\beta$-keto ester enolates with an $\alpha$-halo-substituted hydroximic acid. The resulting esters can be reduced to an alcohol with a metal hydride reducting agent such as DIBAL.

Hydroxystilbenes can be prepared by Horner-Wadsworth-Emmons coupling of an aryl aldehyde and an arylmethylene phosphonate ester, or by Heck coupling of a styrene with an arylbromide, iodide, or triflate in the presence of a palladium catalyst. Using standard chemical methods, tritium or iodine 125 can be incorporated into the compounds of formula (I) and (II).

The compounds of Formula (I) or (II) and their pharmaceutically acceptable derivatives are conveniently administered in the form of pharmaceutical compositions. Thus, in another aspect of the invention, we provide a pharmaceutical composition comprising a compound of formula (I) or (II) or a pharmaceutically acceptable derivative thereof adapted for use in human or veterinary medicine. Such compositions may conveniently be presented for use in conventional manner in admixture with one or more physiologically acceptable carriers or excipients.

The compounds of Formula (I) or (II) and their pharmaceutically acceptable derivatives may be formulated for administration in any suitable manner. They may, for example, be formulated for topical administration or administration by inhalation or, more preferably, for oral, transdermal or parenteral administration. The pharmaceutical composition may be in a form such that it can effect controlled release of the compounds of Formula (I) and (II) and their pharmaceutically acceptable derivatives. A particularly preferred method of administration, and corresponding formulation, is oral administration.

For oral administration, the pharmaceutical composition may take the form of, and be administered as, for example, tablets (including sub-lingual tablets) and capsules (each including timed release and sustained release formulations), pills, powders, granules, elixirs, tinctures, emulsions, solutions, syrups or suspensions prepared by conventional means with acceptable excipients.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules can be made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention can also be administered in the form of liposome emulsion delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The present invention includes pharmaceutical compositions containing 0.1 to 99.5%, more particularly, 0.5 to 90% of a compound of the formula (II) in combination with a pharmaceutically acceptable carrier.

Likewise, the composition may also be administered in nasal, ophthalmic, otic, rectal, topical, intravenous (both bolus and infusion), intraperitoneal, intraarticular, subcutaneous or intramuscular inhalation or insufflation form, all using forms well known to those of ordinary skill in the pharmaceutical arts.

For transdermal administration, the pharmaceutical composition may be given in the form of a transdermal patch, such as a transdermal iontophoretic patch.

For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilizing and/or dispersing agents. For administration by injection these may take the form of a unit dose presentation or as a multidose presentation preferably with an added preservative. Alternatively for parenteral administration the active ingredient may be in powder form for reconstitution with a suitable vehicle.

The compounds of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

Alternatively the composition may be formulated for topical application, for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

The pharmaceutical compositions generally are administered in an amount effective for treatment or prophylaxis of a specific condition or conditions. Initial dosing in human is accompanied by clinical monitoring of symptoms, such symptoms for the selected condition. In general, the compositions are administered in an amount of active agent of at least about 100 µg/kg body weight. In most cases they will be administered in one or more doses in an amount not in excess of about 20 mg/kg body weight per day. Preferably, in most cases, dose is from about 100 µg/kg to about 5 mg/kg body weight, daily. For administration particularly to mammals, and particularly humans, it is expected that the daily dosage level of the active agent will be from 0.1 mg/kg to 10 mg/kg and typically around 1 mg/kg. It will be appreciated that optimum dosage will be determined by standard methods for each treatment modality and indication, taking into account the indication, its severity, route of administration, complicating conditions and the like. The physician in any event will determine the actual dosage which will be most suitable for an individual and will vary with the age, weight and response of the particular individual. The effectiveness of a selected actual dose can readily be determined, for example, by measuring clinical symptoms or standard anti-inflammatory indicia after administration of the selected dose. The above dosages are exemplary of the average case. There can, of course, be individual instances where higher or lower dosage ranges are merited, and such are within the scope of this invention. For conditions or disease states as are treated by the present invention, maintaining consistent daily levels in a subject over an extended period of time, e.g., in a maintenance regime, can be particularly beneficial.

By "therapeutically effective amount" is meant a symptom-alleviating or symptom-reducing amount, a cholesterol-reducing amount, a fatty acid absorption-blocking amount, a protein and/or carbohydrate digestion-blocking amount and/or a de novo cholesterol biosynthesis-blocking amount of a compound. Such amounts can be readily determined by standard methods, such as by measuring cholesterol levels or observing alleviation of clinical symptoms. For example, the clinician can monitor accepted measurement scores for treatments for these diseases, disorders and conditions.

The abbreviations used in the examples are included below.

| ACTR | Activator for Thyroid Hormone and Retinoid Receptors |
|---|---|
| AIB1 | Amplified in Breast Cancer |
| APC | Allophycocyanin |
| APMSF | p-Amidinophenylmethylsulfonylfluoride, HCl |
| Bestatin | [(2S,3R)-3-Amino-2-hydroxy-4-phenylbutanoyl]-Leucine |
| BSA | bovine serum albumin |
| CHAPS | (3-[3-Cholamidopropyl)-dimethylammonio]-1-propanesulfonate |
| CPM | counts per minute |
| DMSO | dimethylsulfoxide |
| DTT | dithiothreitol |
| EDTA | Ethylenediaminetetraacetic acid |
| FXR | Farnasoid X Receptor |
| IBTG | isopropylβ-D-thiogalactopyranoside |
| LBD | ligand binding domain |
| LXR | Liver X Receptor |
| $OD_{600}$ | optical density at 600 nm |
| PBS | phosphate buffered saline [100 mM NaPhosphate, pH 7.2, 50 mM NaCl] |
| pCIP | Co-Integrator Protein |
| RAC | Receptor Activated Cofactor |
| RPM | revolutions per minute |
| RXR | Retinoid X Receptor |
| SA-APC | Streptavidin Crosslinked Allophycocyanin |
| SPA | Scintillation Proximity Assay |
| SRC | Steroid Receptor Cofactor |
| TIF | Transcriptional Intermediary Factor |
| Tris | tris-(Hydroxymethyl)-aminomethane |

The following references are noted and the entire disclosure of each is herein incorporated by reference 1. Apfel., R. H., Benbrook; D., Lernhardt, E., Ortiz, M. A., Salbert, G. And Pfahl, M. "A novel orphan receptor specific for a subset of TREs and its interaction with the retinoid/thyroid hormone receptor superfamily" Mol. Cell. Biol. 14, 7025–7035 (1994)
2. Willy P J. Umesono K. Ong E S. Evans R M. Heyman R A. Mangelsdorf D J. "LXR, a nuclear receptor that defines a distinct retinoid response pathway" Genes & Development. 9:1033–45 (1995)
3. Shinar, D. M., Endo, N., Rutledge, S. J., Vogel, R., Rodan, G. A. and Schmidt, A. "NER, a new member of the gene family encoding the human steroid hormone nuclear receptor" Gene 147, 273–276 (1994)
4. Janowski B A. Willy P J. Devi T R. Falck J R. Mangelsdorf D J. "An oxysterol signalling pathway mediated by the nuclear receptor LXR alpha" Nature.383: 728–31, (1996)
5. Lehmann J M. Kliewer S A. Moore L B. Smith-Oliver T A. Oliver B B. Su J L. Sundseth S S. Winegar D A. Blanchard D E. Spencer T A. Willson T M. "Activation of the nuclear receptor LXR by oxysterols defines a new hormone response pathway" Journal of Biological Chemistry. 272: 3137–40 (1997)
6. Mangelsdorf, D. J. and Evans, R. M. "The RXR Heterodimers and Orphan Receptors" Cell 83: 841–850 (1995)
7. Mukherjee R, Davies, P. J., Crombie, D. L., Bischoff, E. D., Cesario, R. M., Jow, L., Hamann, L. G., Boehm, M. F., Mondon, C. E., Nadzan, A. M., Patemiti Jr., J. R., and Heyman R. A. Sensitization of diabetic and obese mice to insulin by retinoid X receptor agonists. Nature 386: 407–410 (1997)
8. Forman B M. Goode E. Chen J. Oro A E. Bradley D J. Perlmann T. Noonan D J. Burka L T. McMorris T. Lamph W W. et al "Identification of a nuclear receptor that is activated by farnesol metabolites" Cell 81:687–693 (1995)
9. C. K. Glass, D. W. Rose, M. G. Rosenfeld, *Curr. Opin. Cell Biol.* 9, 222 (1997); D. Moras and H. Gronemeyer, *Curr. Opin. Cell Biol.* 10, 384 (1998).
10. B. Le Douarin et al., *EMBO J*. 15, 6701 (1996); D. M. Heery, E. Kalkhoven, S. Hoare, M. G. Parker, *Nature* 387, 733 (1997); G. Krey et al., *Mol. Endocrinol*. 11, 779 (1997).
11. E. Soini, I. Hemmila, P. Dahlen, *Ann. Biol. Clin*. 48, 567 (1990); E. F. Gudgin Dickson, A. Pollak, E. P. Diamandis, *J. Photochem. Photobiol*. 27, 3 (1995).
12. G. Zhou et al., *Mol. Endocrinol*. 12, 1594 (1998); L. Paige et al., *Proc. Natl. Acad. Sci USA*. 96, 3999 (1999).
13. Bouscarel, B., Kroll, S. D., and Fromm, H. (1999). Signal transduction and hepatocellular bile acid transport: cross talk between bile acids and second messengers. Gastroenterology 117, 433–452.
14. Grober, J., Zaghini, I., Fujii, H., Jones, S. J., Kliewer, S. A., Willson, T. M., Ono, T., and Besnard, P. (1999). Identification of a bile acid-responsive element in the human ileal bile acid-binding protein. J. Biol. Chem. 274, 29749–29754.
15. Iser, J. H., and Sali, H. (1981). Chenodeoxycholic acid: a review of its pharmacologic properties and therapeutic use. Drugs 21, 90–119.
16. Johansson, L., Thomsen, J. S., Damdimopoulos, A. E., Spyrou, G., Gustafsson, J.-A., and Treuter, E. (1999). The orphan nuclear receptor SHP inhibits agonist-dependent transcriptional activity of estrogen receptors ERα and ERβ. J. Biol. Chem. 274, 345–353.

17. Makishima, M., Okamoto, A. Y., Repa, J. J., Tu, H., Learned, M., Luk, A., Hull, M. V., Lustig, K. D., Mangelsdorf, D. J., and Shan, B. (1999). Identification of a nuclear receptor for bile acids. Science 284, 1362–1365.
18. Masuda, N., Yasumo, H., Tamura, T., Hashiguchi, N., Furusawa, T., Tsukamoto, T., Sadano, H., and Osumi, T. (1997). An orphan nuclear receptor lacking a zinc-finger DNA-binding domain: interaction with several nuclear receptors. Biochim. Biophys. Acta 1350, 27–32.
19. Parks, D. J., Blanchard, S. G., Bledsoe, R. K., Chandra, G., Consler, T. G., Kliewer, S. A., Stimmel, J. B., Willson, T. M., Zavacki, A. M., Moore, D. D., and Lehmann, J. M. (1999). Bile acids: natural ligands for an orphan nuclear receptor. Science 284, 1365–1368.
20. Rodriguez, M. M., Ron, D., Touhara, K., Chen, C. H., and Mochly-Rosen, D. (1999). RACK1, a protein kinase C anchoring protein, coordinates the binding of activated protein kinase C and select pleckstrin homology domains in vitro. Biochemistry 38, 13787–13794.
21. Russell, D. W. (1999). Nuclear orphan receptors control cholesterol catabolism. Cell 97, 539–542.
22. Seol, W., Choi, H.-S., and Moore, D. (1995). Isolation of proteins that interact specifically with the retinoid X receptor: two novel orphan receptors. Mol. Endocrinol. 9, 72–85.
23. Seol, W., Choi, H.-S., and Moore, D. D. (1996). An orphan nuclear hormone receptor that lacks a DNA binding domain and heeterodimerizes with other receptors. Science 272, 1336–1339.
24. Wang, H., Chen, J., Hollister, K., Sowers, L. C., and Forman, B. M. (1999). Endogenous bile acids are ligands for the nuclear receptor FXR/BXR. Mol. Cell 3, 543–553.
25. Goldstein, J. L. and Brown, M. S., *Nature* 343: 425–430 (1990).
26. Lehmann, J. M. et al. *J.Biol.Chem.* 270: 12953 (1995).
27. 27. Zavacki, A.-M. et al. *Proc. Natl. Acad. Sci. USA* 94: 7909 (1997).
28. 28. Fujita, M. et al. *Eur. J. Biochem.* 233: 406–413 (1995).
29. Mathis, G. (1993) *Clin. Chem.* 39, 1953–1959.

What is claimed is:

1. A method of lowering serum triglycerides in a mammal comprising administering to a mammal in need thereof an effective serum triglyceride lowering amount of a nonsteroidal agonist for Farnesoid X Receptor of the following formula:

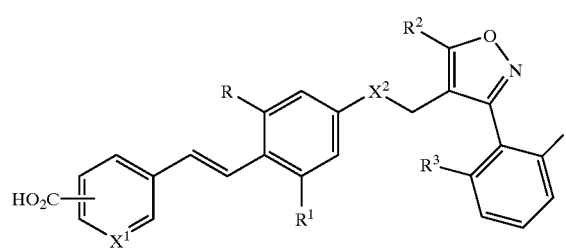

wherein $X^1$ is CH, N; $X^2$ is O or NH; R and $R^1$ are independently H, lower alkyl, halogen, or $CF_3$; $R^2$ is lower alkyl; $R^3$ and $R^4$ are independently H, lower alkyl, halogen, $CF_3$, OH, O-alkyl, or O-polyhaloalkyl.

2. The method of claim 1, wherein said FXR agonist has the following formula:

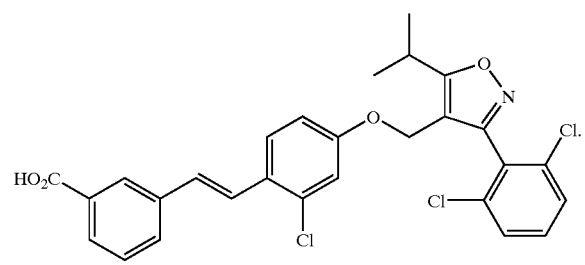

* * * * *

SEQUENCE LISTING

```
<160> NUMBER OF SEQ ID NOS: 6

<210> SEQ ID NO 1
<211> LENGTH: 25
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 1

Cys Pro Ser Ser His Ser Ser Leu Thr Glu Arg His Lys Ile Leu His
1               5                   10                  15

Arg Leu Leu Gln Glu Gly Ser Pro Ser
            20                  25

<210> SEQ ID NO 2
<211> LENGTH: 25
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 2

Gln Glu Gln Leu Ser Pro Lys Lys Lys Glu Asn Asn Ala Leu Leu Arg
1               5                   10                  15

Tyr Leu Leu Asp Arg Asp Asp Pro Ser
            20                  25

<210> SEQ ID NO 3
<211> LENGTH: 25
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 3

Gln Glu Pro Val Ser Pro Lys Lys Lys Glu Asn Ala Leu Leu Arg Tyr
1               5                   10                  15
```

```
Leu Leu Asp Lys Asp Asp Thr Lys Asp
            20              25

<210> SEQ ID NO 4
<211> LENGTH: 27
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 4

Gly Ser Thr His Gly Thr Ser Leu Lys Glu Lys His Lys Ile Leu His
1               5                   10                  15

Arg Leu Leu Gln Asp Ser Ser Ser Pro Val Asp
            20                  25

<210> SEQ ID NO 5
<211> LENGTH: 27
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 5

Ser Asn Met His Gly Ser Leu Leu Gln Glu Lys His Arg Ile Leu His
1               5                   10                  15

Lys Leu Leu Gln Asn Gly Asn Ser Pro Ala Glu
            20                  25

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: synthetic
      peptide motif
<220> FEATURE:
<221> NAME/KEY: MOD_RES
<222> LOCATION: (2)..(3)
<223> OTHER INFORMATION: any amino acid

<400> SEQUENCE: 6

Leu Xaa Xaa Leu Leu
1               5
```